US007786147B2

(12) United States Patent
Buccafusco et al.

(10) Patent No.: US 7,786,147 B2
(45) Date of Patent: Aug. 31, 2010

(54) ANALOGS OF CHOLINE FOR NEUROPROTECTION AND COGNITIVE ENHANCEMENT IN NEURODEGENERATIVE DISORDERS

(75) Inventors: Jerry J. Buccafusco, Evans, GA (US); Alvin V. Terry, Martinez, GA (US); J. Warren Beach, Hoschton, GA (US); Rammamohanna R. Jonnala, Miami, FL (US)

(73) Assignees: Medical College of Georgia Research Institute., Athens, GA (US); University of Georgia Research Foundation, Inc., Athens, GA (US)

( * ) Notice: Subject to any disclaimer, the term of this patent is extended or adjusted under 35 U.S.C. 154(b) by 597 days.

(21) Appl. No.: 11/075,473

(22) Filed: Mar. 9, 2005

(65) Prior Publication Data
US 2005/0227993 A1    Oct. 13, 2005

Related U.S. Application Data

(62) Division of application No. 10/199,205, filed on Jul. 18, 2002, now Pat. No. 6,881,738.

(60) Provisional application No. 60/306,585, filed on Jul. 19, 2001.

(51) Int. Cl.
*C07D 401/02* (2006.01)
*C07D 401/06* (2006.01)
*A61K 31/4439* (2006.01)

(52) U.S. Cl. .................. 514/340; 546/304; 546/329; 514/352; 514/357

(58) Field of Classification Search ................ 546/304, 546/329; 514/340, 352, 357
See application file for complete search history.

(56) References Cited

U.S. PATENT DOCUMENTS

| | | | |
|---|---|---|---|
| 2,833,770 | A | 5/1958 | Parcell et al. |
| 3,133,061 | A | 5/1964 | Kirchner |
| 3,705,899 | A | 12/1972 | Regnier et al. |
| 3,749,725 | A | 7/1973 | Freed et al. |
| 3,862,938 | A | 1/1975 | Lunsford et al. |
| 4,421,753 | A | 12/1983 | Tomcufcik et al. |
| 5,120,843 | A | 6/1992 | McCall et al. |
| 5,242,934 | A | 9/1993 | Lippiello et al. |
| 5,260,293 | A | 11/1993 | Baker et al. |
| 5,486,527 | A | 1/1996 | Alker et al. |
| 5,616,707 | A | 4/1997 | Crooks et al. |
| 5,731,309 | A | 3/1998 | Bernstein et al. |
| 5,965,555 | A | 10/1999 | Gebert et al. |
| 6,881,738 | B2 | 4/2005 | Buccafusco et al. |

FOREIGN PATENT DOCUMENTS

FR          2699173      6/1994

OTHER PUBLICATIONS

Seeman et al. Journal of Organic Chemistry, 1986, 51, 1548-1551.*
Chelucci et al. Journal of Molecular Catalysis A: Chemical 130 (1998) 51-55.*
Aronstam RS et al. 1982. Neurosci Letts 28:51-56.
Aronstam RS et al. 1988. Neuropharmacology 27:217-225.
Benishin CG et al. 1981. J Neurochem 36:732-740.
Barker LA et al. 1975. J Pharmacol Exp Ther 192:86-94.
Boksa P et al. 1980. J Neurochem 35:1099-1104.
Buccafusco JJ et al. 1981. Neurosci Letts 23:319-324.
Buccafusco JJ et al. 1988. Neuropharmacology 27:227-233.
Gebber GL et al. 1965. J Pharmacol Exp Ther 150:67-74.
Kmjevic K et al 1979. Science 206:1321-1323.
Large WA et al. 1978. J Physiol 285:1-24.
Meyer EM et al. 1982. J Neurochem 39:321-326.
Naves LA et al. 1996. Brain Res 730:58-66.
Newton MW et al. 1985. J Pharmacol Exp Ther 235:135-146.
Papke RL et al. 1996. Neurosci Letts 213:201-204.
Papke RL et al. 2000. Eur J Pharmacol 393:179-195.
Patterson TA et al. 1989. Brit J. Pharmacol 97:451-460.
Strahlendorf JC et al. 2001. Brain Res 901:71-78.
Thomas JD et al. 2000. Neurotoxicol Teratol 22: 703-711.
Von Schwarzenfeld I et al. 1977. Brit J Pharmacol 59:69-74.
Alkondon M, Pereira EFR, Cortes WS, Maelicke A and Albuquerque EX, 1997. Eur J. Neurosci 9: 2734-2742.
Alkondon M, Braga MFM, Pereira EFR, Maelicke A and Albuquerque EX. 2000. Eur J Pharmacol 393: 59-67.
Jenden DJ, Russell RW, Booth RA, Laurentz SD, Knusel BJ, Roch M, Rice KM, George R and Waite JJ, 1987. J Neural Transmission, Suppl 24: 325-329.

(Continued)

*Primary Examiner*—Kahsay T Habte
(74) *Attorney, Agent, or Firm*—Henry D. Coleman; R. Neil Sudol; William J. Sapone

(57) ABSTRACT

The present invention relates to novel analogs of choline and methods of use or treatment of neurodegenerative disorders and/or conditions such as Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), dementia with Lewy bodies, schizophrenia, paraneoplastic cerebellar degeneration and neurodegenerative conditions caused by stroke. The present compounds are effective to treat any neurological condition where acetylcholine transmission neurons and their target cells are affected. Compounds according to the present invention are effective to alleviate and/or reverse the effects of a neurodegenerative condition, prevent further deterioration and/or enhance cognition and memory in patients suffering from neurodegenerative disorders, especially Alzheimer's disease.

27 Claims, 14 Drawing Sheets

OTHER PUBLICATIONS

Jenden DJ, Russell RW, Booth RA, Knusel BJ, Lauretz SD, Rice KM and Roch M, 1989. EXS 57: 229-235.
Kilbinger H, Wagneer A and Zerban R. 1976. Naunyn-Schmiedeberg's Arch Pharmacol 295: 81-87.
Matthews RT and Chiou CY. 1979. Eur J. Pharmacol 56: 159-165.
Tees RD and Mohammadi E. 1999. Dev Psychobiol 35: 226-240.
Perez et al., Tetrahedron Letters, vol. 37, No. 47, pp. 8487-8488, 1996.
STN Computer Prinitout of Duhamel et al. Sciences Chimiques 1973. 276(15), 1319-22.
Yutaka et al. Organometallics 1997, 16(16), 3615-3622.
Abstract of Martirosyan et al., Izvestiya Akademii Nauk Armyanskoi SSR, Khmicheskie Nauk (1964), 17(5), 517-521.
Xiao, Yingxian et al., "Sazetidine-A, A Novel Ligand That Desensitizes Alpha4Beta4 Nicotinic Acetylcholine Receptors without Activating Them" Molecular Pharmacology 70:1454-1460, 2006.
Zwart, Rudd et al., "Sazetidine-A Is a Potent and Selective Agonist at Native and Recombinant Alpha4Beta2 Nicotinic Acetylcholoine Receptors" Molecular Pharmacology 73:1838-1843, 2008.
SciFinder Scholar, Jul. 24, 2008, Chemical Structure Search in Caplus and Medline.
Andraos, John, "Quantification and Optimization of Dynamic Kinetic Resolution" Journal of Physical Chemistry A (2003), 107(13). 2374-2387. Abstract only.
Wang, David X. et al. "Structure-activity relationships for nicotine analogs comparing competition for [3H]nicotine binding and psychotropic potency." Drug Development Research (1998), 45(1), 10-16. Abstract only.
Seeman, J. I. et al., "Separation of homologous and isomeric alkaloids related to nicotine on a beta-cyclodextrin-bonded phase." Journal of Chromatography (1989), 483: 169-77. Abstract only.
Seeman, J.I. et al., "Enantiometric resolution and chiral recognition of racemic nicotine and nicotine analogs by beta-cyclodextrin complexation. Structure-enantiomeric resolution relationships in host-guest interactions." Analytical Chemistry (1988), 60(19), 2120-7. Abstract only.
Romano, Carmelo et al., ""Characterization of the receptor mediation the nicotine discriminative stimulus. Psychopharmacology (Berlin, Geermany) (1981), 74(4), 310-15. Abstract only.
Rondahl, Lars, et al., "Synthetic analogs of nicotine. VII. Acid dissociation constants of some nicotine analogs." Acta Pharmaceutica Suecica (1979), 16(1), 56-63. Abstract only.
Sugasawa, Shigehiko et al., "A synthesis of dl-4-(N-methylpyrrolid-2-yl)pyridine." Pharmaceutical Bulletin (1954), 2:37-9. Abstract only.
Seeman, J.K. et al., "Preparation of Hydroxyalkyl-Substituted Nicotinoids" J. Org. Chem. 1986, 51:1548-1551.

* cited by examiner

Scheme 1

Scheme 2

Scheme 3

Synthesis of Pyridylpiperazine Compounds

SCHEME 4

MTT Reduction Assay

Displacement of Cell Surface [$^{125}$I]α-Bungarotoxin Binding to Differentiated PC-12 Cells

- ● Nicotine (Ki = 1.24 μM)
- ○ Choline (Ki = 61.1 μM)

Displacement of Cell Surface [$^{125}$I]α-Bungarotoxin Binding to Differentiated PC-12 Cells ● Pyrrolidinecholine (Ki = 27.2 μM)
○ Benzylcholine 26 (Fig 4)

N-(hydroxyethyl)piperazine HCl 2 (Fig 3)

ANALOGS OF CHOLINE FOR NEUROPROTECTION AND COGNITIVE ENHANCEMENT IN NEURODEGENERATIVE DISORDERS

RELATED APPLICATIONS

This application is a divisional application of Ser. No. 10/199,205, filed Jul. 21, 2002, now U.S. Pat. No. 6,881,738, which claims priority from provisional application no. 60/306,585, filed Jul. 19, 2001, both of which applications are incorporated by reference herein in their entirety.

FIELD OF THE INVENTION

The present invention relates to novel analogs of choline and methods of use or treatment of neurodegenerative disorders such as Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), dementia with Lewy bodies, schizophrenia, paraneoplastic cerebellar degeneration and neurodegenerative conditions caused by stroke. The present compounds are effective to treat any neurological condition where acetylcholine transmission neurons and their target cells are affected. Compounds according to the present invention are effective to alleviate and/or reverse the effects of a neurodegenerative condition, prevent further deterioration and/or enhance cognition and memory in patients suffering from neurodegenerative disorders, especially Alzheimer's disease.

BACKGROUND OF THE INVENTION

As the population ages, the frequency with which patients are diagnosed with neurodegenerative diseases, especially those which affect mental faculties such as Alzheimer's, is growing dramatically. The number of individuals having Alzheimer's disease is growing exponentially and it is estimated that today there may be as many as 24 million individuals worldwide afflicted with this condition.

Alzheimer's Disease (AD) is caused by a degenerative process in the patient which is characterized by progressive loss of cells from the basal forebrain, cerebral cortex and other brain areas. Acetylcholine transmitting neurons and their target nerves are particularly affected. Senile plaques and neurofibrillary tangles are present. Pick's disease has a similar clinical picture to Alzheimer's disease but a somewhat slower clinical course and circumscribed atrophy, mainly affecting the frontal and temporal lobes. One animal model for Alzheimer's disease and other dementias displays hereditary tendency toward the formation of such plaques. It is thought that if a drug has an effect in the model, it also may be beneficial in at least some forms of Alzheimer's and Pick's diseases. At present there are palliative treatments but no means to restore function in Alzheimer's patients.

Parkinson's disease (PD), is a disorder of middle or late life, with very gradual progression and a prolonged course. HARRISON'S PRINCIPLES OF INTERNAL MEDICINE, Vol. 2, 23d ed., Ed by Isselbacher, Braunwald, Wilson, Martin, Fauci and Kasper, McGraw-Hill Inc., New York City, 1994, pg. 2275. The most regularly observed changes in patients with Parkinson's disease have been in the aggregates of melanin-containing nerve cells in the brainstem (substantia nigra, locus 20 coeruleus), where there are varying degrees of nerve cell loss with reactive gliosis (most pronounced in the substantia nigra) along with distinctive eosinophilic intracytoplasmic inclusions. (Id. at 2276). In its fully developed form, PD is easily recognized in patients, where stooped posture, stiffness and slowness of movement, fixity of facial expression, rhythmic tremor of the limbs, which subsides on active willed movement or complete relaxation, are common features. Generally, accompanying the other characteristics of the fully developed disorder is the festinating gait, whereby the patient, progresses or walks with quick shuffling steps at an accelerating pace as if to catch up with the body's center of gravity. (Id. At 2276).

The treatment of Parkinson's disease pharmacologically with levodopa combined with stereotactic surgery has only represented a partial cure, at best. (Id at 2277). Underlying much of the treatment difficulty is directed to the fact that none of these therapeutic measures has an effect on the underlying disease process, which consists of neuronal degeneration. Ultimately, a point seems to be reached where pharmacology can no longer compensate for the loss of basal ganglia dopamine. (Id.).

A group of related neuronal degenerative disorders is characterized by progressive ataxia due to degeneration of the cerebellum, brainstem, spinal cord and peripheral nerves, and occasionally the basal ganglia. Many of these syndromes are hereditary; others occur sporadically. The spinocerebellar degenerations are logically placed in three groups: predominantly spinal ataxias, cerebellar ataxias and multiple-system degenerations. To date there are no treatments. Friedrich's ataxia is the prototypical spinal ataxia whose inheritance is autosomal recessive. The responsible gene has been found on Chromosome 9. Symptoms begin between ages of 5 and 15 with unsteady gait, followed by upper extremity ataxia and dysarthria. Patients are flexic and lose large-fiber sensory modalities (vibration and position sense). Two other diseases have similar symptoms: Bassen-Kornzweig syndrome (abeta-lipoproteinemia and vitamin E deficiency) and Refsom's disease (phytanic acid storage disease). Cerebellar cortical degenerations generally occur between ages 30 and 50. Clinically only signs of cerebellar dysfunction can be detected, with pathologic changes restricted to the cerebellum and occasionally the inferior olives. Inherited and sporadic cases have been reported. Similar degeneration may also be associated with chronic alcoholism. In multiple-system degenerations, ataxia occurs in young to middle adult life in varying combinations with spasticity and extrapyramidal, sensory, lower motor neuron and autonomic dysfunction. In some families, there may also be optic atrophy, retinitis pigmentosa, opthalmoplegia and dementia.

Another form of cerebellar degeneration is paraneoplastic cerebellar degeneration that occurs with certain cancers, such as oat cell lung cancer, breast cancer and ovarian cancer. In some cases, the ataxia may precede the discovery of the cancer by weeks to years. Purkinje cells are permanently lost, resulting in ataxia. Even if the patient is permanently cured of the cancer, their ability to function may be profoundly disabled by the loss of Purkinje cells. There is no specific treatment. Stroke often also results in neuronal degeneration and loss of functional synapses.

OBJECT OF THE INVENTION

It is an object of the invention to provide novel choline analogs which can be used to treat neurological conditions where acetylcholine transmission neurons and their target cells are affected.

It is another object of the invention to provide pharmaceutical compositions which may be used to treat any one or more neurodegenerative disease and conditions including, for example, Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, dementia with Lewy bodies, schizophrenia, paraneoplastic cerebellar degeneration and neurodegenerative conditions caused by stroke.

It is still another object of the invention to provide compositions and methods which are effective to reverse the effects of a neurodegenerative condition, prevent further deterioration and/or enhance cognition and memory in patients suffering from neurodegenerative disorders, especially including Alzheimer's disease.

One or more of these and/or other objects of the present invention may be readily gleaned from the description of the invention which follows.

SUMMARY OF THE INVENTION

Figure 1:
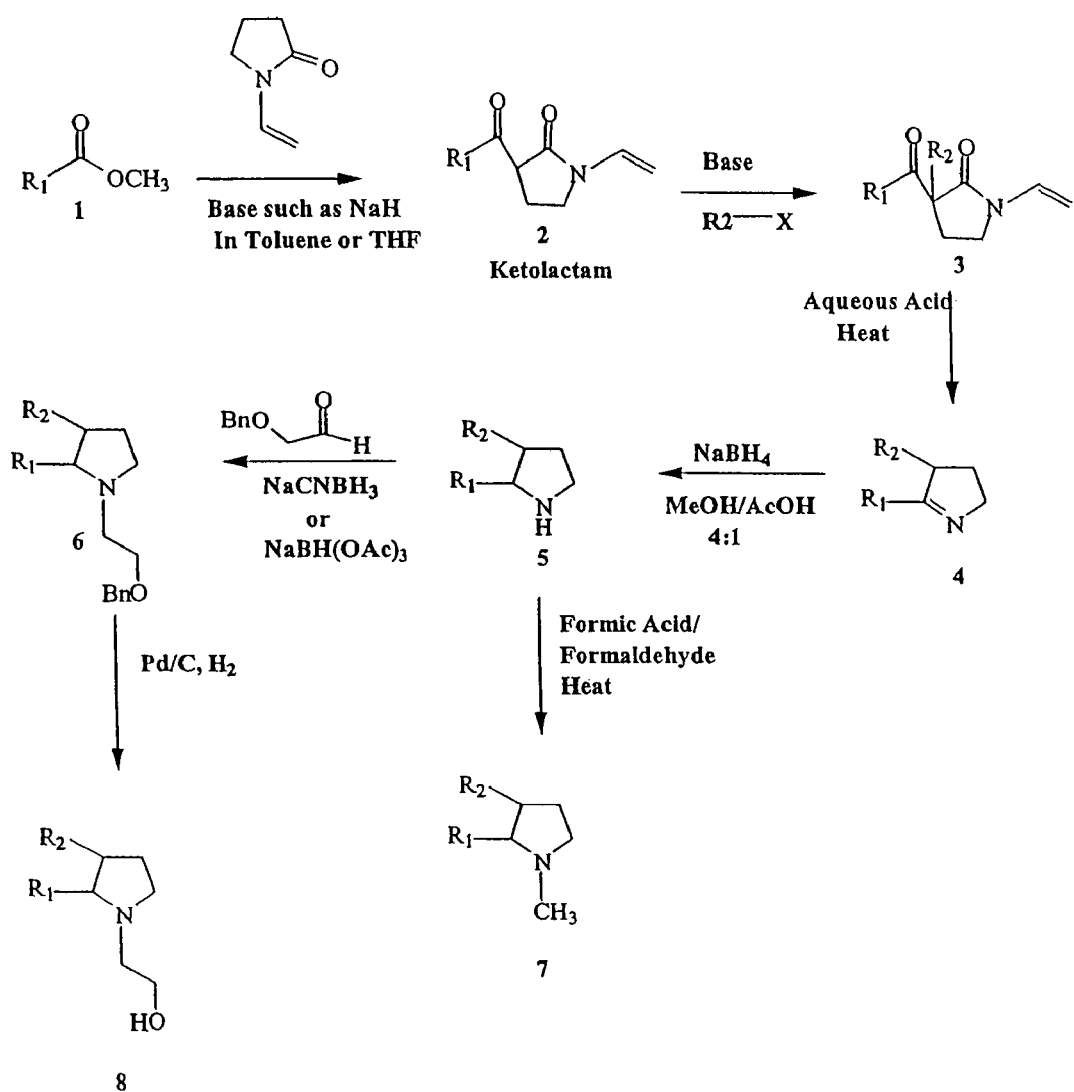
FIGS. 1-4 are representative of synthetic chemical schemes which may be used to prepare compounds according to the present invention.
Figure 2:
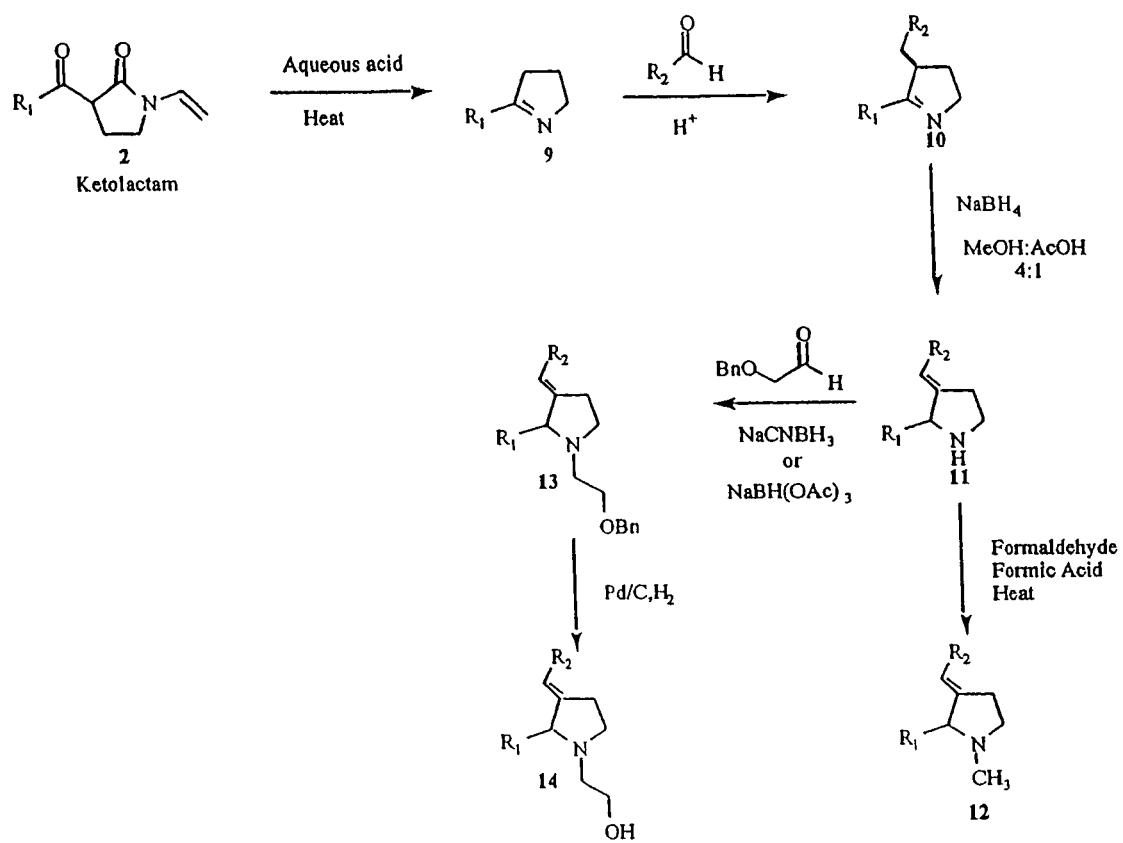

The present invention relates to compounds according to the structures:

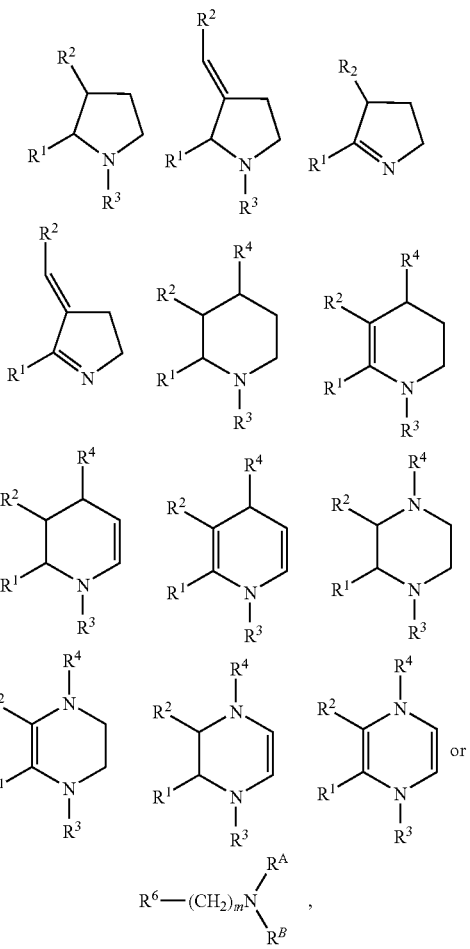

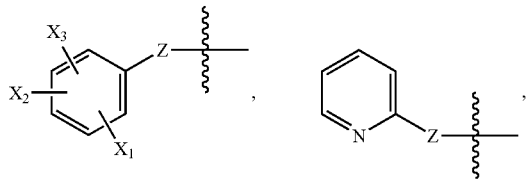

Where each of $R^1$, $R^2$ and $R^4$ is independently selected from H, a $C_1$ to $C_{12}$ straight, branch-chained or cyclic saturated or unsaturated hydrocarbon, a $(CH_2)_nOR^5$ group or an $R^6$ group;

$R^3$ is H, a $C_1$ to $C_{12}$ alkyl or alkene group or a $(CH_2)_nOR^5$ group with the proviso that $R^3$ and $R^4$ are not both H;

$R^A$ and $R^B$ are independently selected from H, a $C_1$ to $C_{12}$ alkyl or alkenyl group or a $(CH_2)_mOR^5$ group, preferably with the proviso that when one of $R^A$ or $R^B$ is a $(CH_2)_mOR^5$ group, the other of $R^A$ or $R^B$ is not a $(CH_2)_mOR^5$ group;

$R^5$ is H or a $C_1$ to $C_{12}$ alkyl, alkenyl group or carboxylic acid, a $C_2$ to $C_{12}$ acyl or alkyl ester group or a $C_3$ to $C_{12}$ alkylene ester group;

$R^6$ is a group according to the structure:

-continued

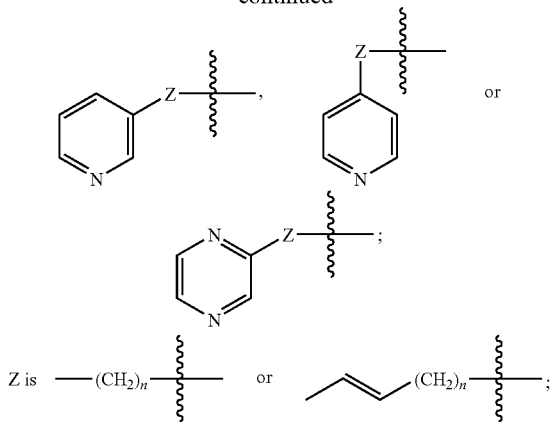

n is 0 to 12, preferably 1 to 8;
m is 1 to 8; and
$X_1, X_2$ and $X_3$ are each independently selected from H, OH, F, Cl, Br, $NO_2$, $R^4$, $OR^4$, $CF_3$ or $OCF_3$;
or a pharmaceutically acceptable salt thereof.

Compounds according to the present invention may be used to produce pharmaceutical compositions for treatment of one or more neurodegenerative diseases or conditions, for example, Parkinson's disease, Huntington disease, Alzheimer's disease and other disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), dementia with Lewy bodies, schizophrenia, paraneoplastic cerebellar degeneration and neurodegenerative conditions caused by stroke. The present compounds are effective to treat any neurological condition where acetylcholine transmission neurons and their target cells are affected. Compounds according to the present invention are effective to reverse the effects of a neurodegenerative condition, prevent further deterioration and/or enhance cognition and memory, especially in patients suffering from neurodegenerative disorders, such as Alzheimer's disease.

Compounds according to the present invention may also be used as biological probes or standards for testing purposes or as intermediates in the synthesis of related compounds having pharmacological activity.

The present invention is also directed to pharmaceutical compositions comprising effective amounts of any one or of the compounds according to the present invention or their pharmaceutically acceptable derivatives, including pharmaceutically acceptable salts, optionally, in combination with a pharmaceutically acceptable additive, carrier or excipient.

The present invention is also directed to methods for the treatment of neurological conditions where acetylcholine transmission neurons and their target cells are affected. Thus, the present compounds may function primarily to reverse and/or prevent deterioration from a neurodegenerative condition. The present compounds may also be used to enhance cognition in memory in patients whose cognition and/or memory is impaired, either due to natural aging processes or to a neurodegenerative condition. In this aspect according to the present invention, the use of pyrrolidine choline or pyrrolidine acetyl choline is preferred.

DETAILED DESCRIPTION OF THE INVENTION

The term "patient" is used throughout the specification to describe an animal, preferably a human, to whom treatment, including prophylactic treatment, with the compositions according to the present invention, is provided. For treatment of those infections, conditions or disease states which are specific for a specific animal such as a human patient, the term patient refers to that specific animal.

The term "neurodegenerative disease" is used throughout the specification to describe a disease or condition of the nervous system in which the nervous system often deteriorates over time, thus impairing the patient from carrying out normal tasks including motor tasks and tasks related to cognition and/or memory. Neurodegenerative diseases which may be treated using compounds according to the present invention include, for example, Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), dementia with Lewy bodies, schizophrenia, paraneoplastic cerebellar degeneration and neurodegenerative conditions caused by stroke, among others. A neurodegenerative disease for purposes of the present invention is any neurological condition where acetylcholine transmission neurons and their target cells are affected, including neurological conditions which are caused by toxins.

The term "treatment", "treating" or "treated" is used throughout the specification to describe a method in which compounds according to the present invention are used to reverse the effects of a neurodegenerative condition, prevent further deterioration and/or enhance cognition and memory, especially in patients suffering from neurodegenerative or neurologicial disorders, such as Alzheimer's disease or those which have been caused by toxins or occurred from natural causes such as aging.

The term "effective amount" is used throughout the specification to mean an amount or concentration of a compound according to the present invention which is effective within the context of its administration, whether that context produces the desired result of alleviating, reversing or preventing further deterioration of the condition or disease state to be treated. Effective amounts of compounds according to the present invention include those amounts which are effective to enhance and/or increase cognition and/or memory in patients in need.

The term "cognitive task" or "cognitive function" is used to describe an endeavor or process by a patient or subject which involves thought or knowing by which animals, particularly humans, come to know the world. Selectively attending to a particular stimulus, recognizing and identifying these relevant stimulus features and planning and experiencing the response are some of the processes or abilities mediated by the human brain which are related to cognition.

The term "memory" is used to describe the faculty of remembering—the power with which an individual reproduces past impressions, e.g., a thought process or visual or sensory information to which a patient has been exposed in the past and which the patient is able to recall, assimilate and use for a purpose in the present.

The term "motor task" is used to describe an endeavor which is taken by a patient or subject which involves movement or action.

The term "perceptual task" is used to describe an act by a patient or subject of devoting attention to sensory inputs.

The term "impaired" where used, describes a function of the neurological system which is working at a level which is less than normal. Impaired functions can be significantly impacted such that a function is barely being carried out, is virtually non-existent or is working in a fashion which is significantly less than normal. The impairment of function will vary in type as well as severity from patient to patient and the condition to be treated.

The term "pharmaceutically acceptable derivative" is used throughout the specification to describe any pharmaceutically acceptable salt or prodrug form which, upon administration to a patient, provides directly or indirectly the compound or an active metabolite of the compound according to the present invention. In general, the free amine form (generally, a secondary or tertiary amine) of compounds according to the present invention readily form salts with organic and/or mineral acids. Pharmaceutically acceptable salts include those derived from pharmaceutically acceptable inorganic or organic bases and acids, generally, in the case of the present invention, inorganic and organic acids (due to the presence of an amine group which may be protonated). Suitable salts preferably include ammonium salts obtained from acidifying amine groups of the compound with organic and inorganic acids well known in the pharmaceutical art.

The term "alkyl" shall mean within its context a fully saturated hydrocarbon which may be linear, branch-chained or cyclic radical within its context, preferably a $C_1$-$C_4$, even more preferably a $C_1$-$C_3$ linear, branch-chained or cyclic fully saturated hydrocarbon radical. The term "alkenyl" is used to describe a hydrocarbon group, similar to an alkyl group which contains one double bond.

The term "acyl" is used to describe a group having a carbonyl group to which is bonded carbon atoms. The term "ester" is used to describe an alkoxy carbonyl group. The term carboxylic acid is used to describe a carboxylic acid or alkylene carboxylic acid group. The terms acyl, ester and carboxylic acid includes alkyl acyl groups, alkyl ester groups, alkylene alkyl acyl groups or alkylene alkyl ester groups of the formula:

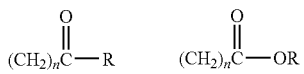

Where n is 0 to 11 and R is H or a $C_1$-$C_{11}$ alkyl group.

Compounds according to the present invention are used to treat neurodegenerative diseases and conditions by alleviating, reversing or preventing further deterioration from diseases or conditions such as Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), paraneoplastic cerebellar degeneration and neurodegenerative conditions caused by stroke. The present compounds may be used to treat any neurological condition where acetylcholine transmission neurons and their target cells are affected.

Methods for treating conditions or disease states as described above comprise administering an effective amount of at least one or more compounds according to the present invention to a patient in need thereof to alleviate, reverse and/or prevent or reduce the likelihood that further deterioration will occur in the condition or disease state which is treated. In the case of treating a patient to improve that patient's memory and/or cognition or prevent further deterioration of memory or cognition, such methods comprise administering to a patient in need thereof an effective amount of one or more of the compounds according to the present invention.

General Chemical Synthesis

The compounds according to the present invention are produced by synthetic methods which are readily known to those of ordinary skill in the art and include various chemical synthetic methods as elaborated in significantly more detail in the Examples which follow. In general, compounds according to the present invention are synthesized by methods which are well-known in the art.

For example, as set forth in Scheme I, the base catalzyed condensation of ester (1) and N-vinylpyrrolidinone may be accomplished under anhydrous reflux conditions in either toluene, tetrahydrofuran or similar aprotic solvent in the presence of strong non-nucleophilic base such as sodium hydride, sodium bis(trimethylsilyl)amide, lithium di-isopropylamide, lithium bis(trimethylsilyl)amide to provide the ketolactam (2). Introduction of an R group at the 3 position of the pyrrolidine ring is accomplished by base generated anion formation followed by alkylation with an R—X (X is a leaving group) company to give compound 3. Treatment of compound 3 with aqueous acid under reflux conditions generates compound 4. Reduction of compound 4 with sodium borohydride in methanol/acetic acid (4:1) at −15 to 0 C yields compound 5. Reductive N-alkylation with benzyloxy aldehyde in the presence of either sodium cyanoborohydride or sodium triacetoxyborohydride (or equivalent conditions) yields compound 6 which is de-benzylated using catalytic hydrogenation to compound 8. Alternatively, compound 5 can be converted to compound 7 by refluxing in a mixture of formic acid and formaldehyde as indicated in Scheme I.

Compounds which contain unsaturation in the pyrrolidine ring or in the side chain on position 3 may be synthesized readily by an alternative route following the steps which are set forth in Scheme II or using any analogous procedure known in the art. The ketolactam (2) is converted to the imine (9) by refluxing in aqueous acid. Reaction of compound (9) with aldehydes under acidic conditions generates compound (10). Reduction of compound (10) with, for example, sodium borohydride, gives compound (11), which undergoes reductive N-alkylation as described above with benzyloxy aldehyde to provide compounds (12) and (14). Other compounds within the scope of the present invention may be readily synthesized by analogy using the above-described general methods and as set forth in the examples section which follows.

Figure 3:
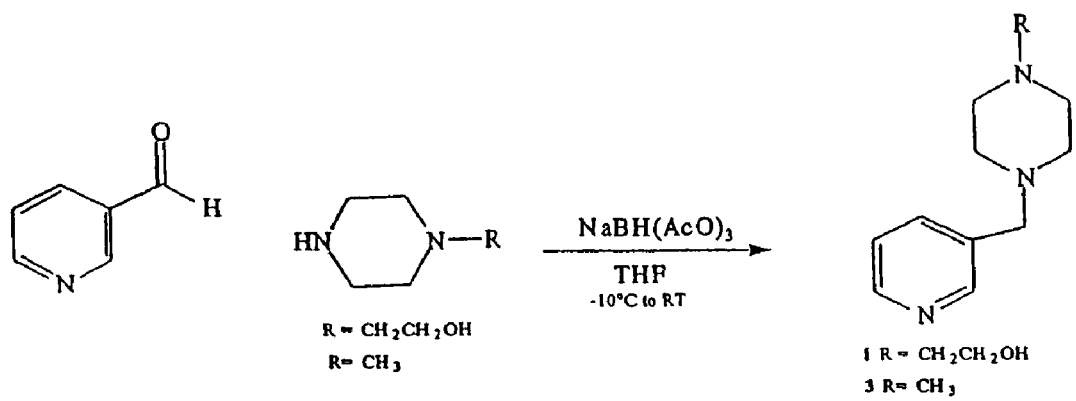
Figure 3:
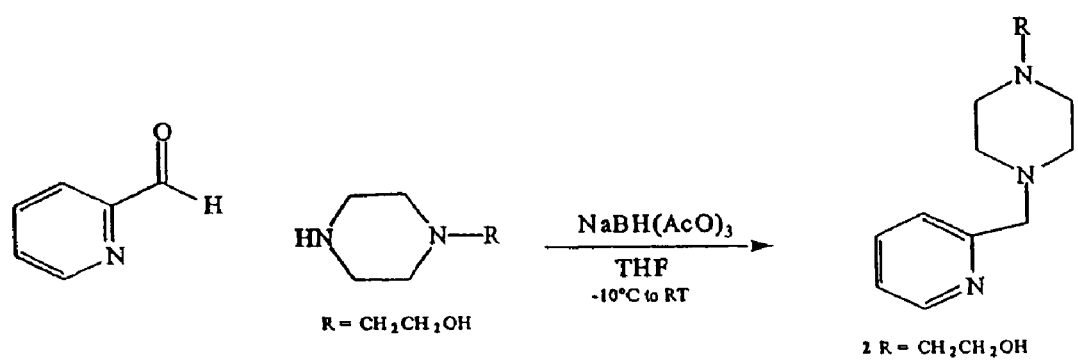

Piperidine, piperazine and other diamine analogs such as pyridylpiperazine compounds of the present invention may be synthesized according to scheme 3 set forth in FIG. 3. Pursuant to scheme 3, the corresponding formyl pyridine analog is reacted with an amine-substituted piperazine compound under condensation conditions (in scheme 3, using for example, NaBH(AcO)$_3$ in the presence of tetrahydrofuran at reduced temperature) to afford the corresponding pyridine-piperazine compound. Analogs with numerous substituents on either the pyridine ring or the piperidine or piperazine (or corresponding unsaturated amine or diamine) ring Other compounds which contain tertiary amine groups pendant to an aryl group, such as benzene are readily synthesized according to synthetic scheme 4 set forth in FIG. 4 or by modifications thereof. See, for example, A. F. Abdel-Magid, K. G. Carson, B. D. Harris, C. A. Marynoff and R. D. Shah, "Reductive Amination of Aldehydes and Ketones with Sodium Triacetoxyborohydride. Studies on Direct and Indirect Reductive Amination Procedures," *J. Org. Chem.*, 61, 3849, (1996).

Figure 4:
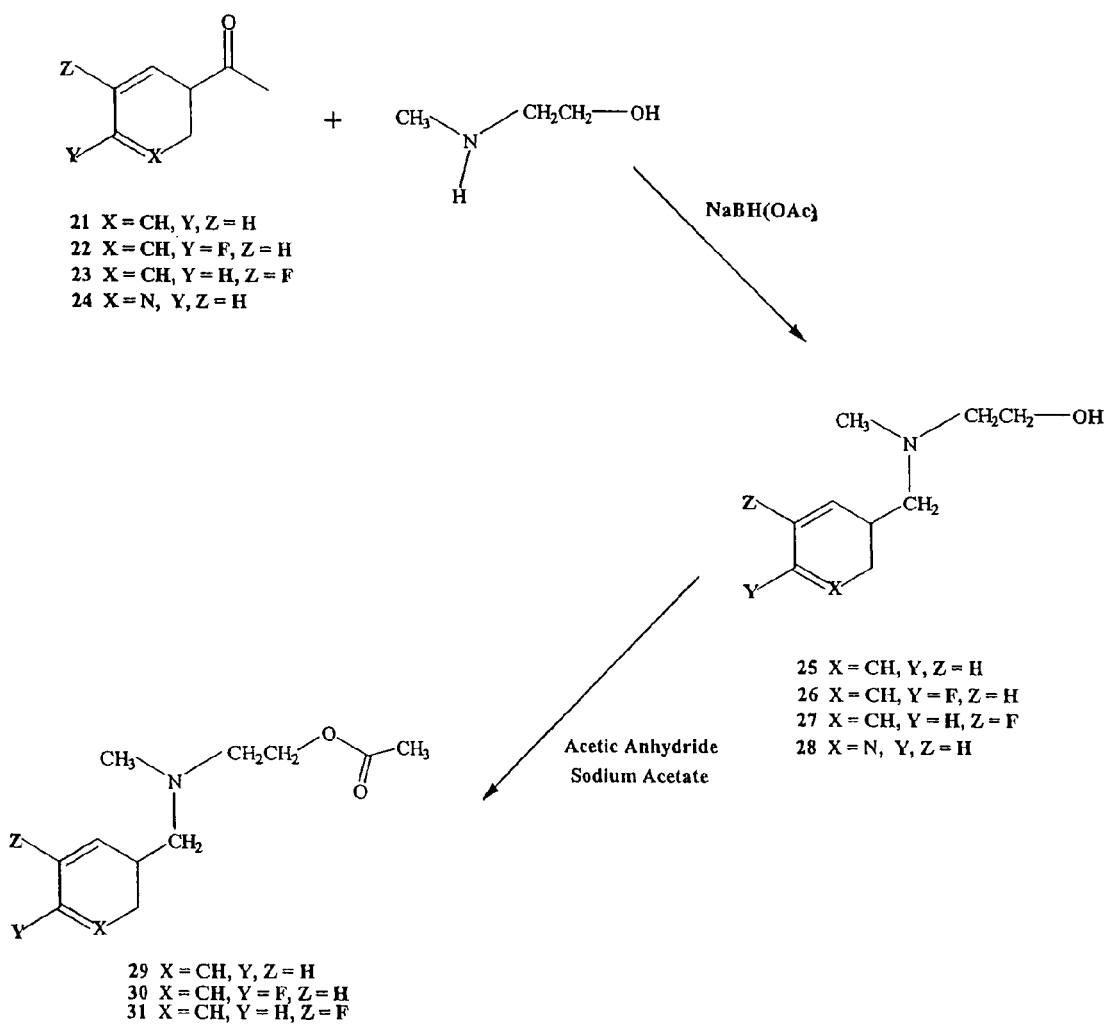

According to the scheme set forth in FIG. 4, the appropriate benzyl or pyridylaldehyde (21-24) is reacted with methylethanolamine to rapidly form the corresponding imine, which is then subjected to reducing conditions in the presence of $NaBH(AcO)_3$ in 1,2-dichloroethane or THF, to form the corresponding benzyl substituted tertiary alkanolamine (25-28), which may readily esterified using standard techniques (for example, acetic anhydride in sodium acetate).

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the desired position of the pyrrolidine ring or related synthon.

Pharmaceutical compositions according to the present invention comprise the above-described compounds in a therapeutically effective amount for treating a neurodegenerative disease or condition or for enhancing or restoring or preventing the deterioration of cognition and/or memory in a patient, optionally in combination with a pharmaceutically acceptable additive, carrier or excipient. One of ordinary skill in the art will recognize that a therapeutically effective amount will vary with the disease or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including ester and ether derivatives, as well as various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition. In general, an effective amount of the present compound in pharmaceutical dosage form usually ranges from about 0.05 mg/kg to about 100 mg/kg or more, more preferably, slightly less than about 0.1 mg./kg. to about 20 mg./kg. of the patient or considerably more, depending upon the compound used, the condition or infection treated and the route of administration. For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to specific antigens such as receptors for more effective delivery to a site within a patient's body) may also be prepared by conventional methods to produce pharmaceutically acceptable carriers. This may be appropriate for the delivery of a number of compounds according to the present invention.

In preferred embodiments according to the present invention, the compounds and compositions are used to treat, prevent or delay the onset of Alzheimer's disease or to improve the memory and/or cognition of patients suffering from Alzheimer's disease. Preferably, to treat, prevent or delay the onset of Alzheimer's disease or its related symptomotology, the compositions according to the present invention will be administered in oral dosage form in amounts ranging from about 250 micrograms up to about 500 mg or more at least once a day, preferably, up to four times a day. The present compounds are preferably administered orally, but may be administered parenterally, topically or in suppository form.

Some of the compounds according to the present invention, because of their low toxicity to host cells, may advantageously be employed prophylactically. In this aspect according to the present invention, the present compositions are used to prevent or delay the onset of a neurodegenerative disease or prevent the patient from further deterioration from the disease. This prophylactic method comprises administering to a patient in need of such treatment or who is at risk for the development of neurodegenerative disease and in particular, Alzheimer's disease, an amount of a compound according to the present invention effective for alleviating, preventing or delaying the onset of the disease. In the prophylactic treatment according to the present invention, it is preferred that the compound utilized should be as low in toxicity and preferably non-toxic to the patient. It is particularly preferred in this aspect of the present invention that the compound which is used should be maximally effective against the disease state and should exhibit a minimum of toxicity to the patient. In the case of the present compound for the prophylactic aspect of the present invention, these compounds may be administered within the same dosage range for therapeutic treatment (i.e., about 250 micrograms up to about 500 mg. or more from one to four times per day for an oral dosage form) as a prophylactic agent to prevent or delay the onset of the symptomotology of the neurodegenerative diseases, and in particular, Alzheimer's disease which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other agents having similar or preferably a different mechanism of action, which may be used for treating neurodegenerative diseases or related conditions. Certain compounds according to the present invention may be effective for enhancing the biological activity of certain agents according to the present invention by reducing the metabolism or inactivation of other compounds and as such, are co-administered for this intended effect.

While not being limited by way of theory or mechanism of action, it is believed that the compounds according to the present invention exhibit their pharmacological activity by acting as agonists of the acetylcholine nicotinic receptor in order to enhance cognition and/or memory or to protect cells against various types of toxic insults.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Chemical Synthesis of Compounds

General procedure for preparation of ketolactam (Brandage and Lindblom, Acta Chem. Scand., 30, 93, 1976 and Bleicher, et al., J. Org. Chem. 63, 1109-1118, 1998) (2) To NaH (1.1 equiv., 1.4 g), rinsed with toluene (3×) to remove mineral oil, stirring in approximately 10 ml toluene was added neat N-vinyl pyrrolidinone 99% (1.1 equiv.). After stirring for 10 mins., ester dissolved in toluene was added dropwise. Upon addition of the ester, an exotherm evolved and the reaction mixture became green in color. After the exotherm subsided, the reaction stirred for an additional 30 mins. at ambient temperature and during this time the color changed to yellow. The reaction was heated to reflux for 15 mins., and slowly cooled to room temperature. Water was poured onto the reaction to dissolve the orange, pasty product. The aqueous layer was washed with diethyl ether, and neutralized with 5% HCl. The neutral aqueous phase was extracted with EtOAc (3×), and the organic extracts pooled and concentrated to yield the crude ketolactam product, which was subsequently used without purification.

3-(1-pyrrolin-2-ylmethyl)pyridine (homomyosmine) (Brandage and Lindblom, Acta Chem. Scand., 30, 93, 1976 and Bleicher, et al., J. Org. Chem. 63, 1109-1118, 1998) To a 500 ml round-bottom flask equipped with a Dean-Stark apparatus and a non-pressure regulated addition funnel was added approximately 200 ml 50% HCl solution. The acid solution was heated to 70° C. and the crude ketolactam product dissolved in approximately 10 ml THF was added dropwise to the stirring acid solution. After addition of 2, the Dean-Stark trap and the addition funnel were removed and a water condenser was connected to the reaction flask. The reaction was heated to reflux for 18 h. After reflux, the reaction mixture had darkened and a tarry byproduct had formed on the vessel wall. The reaction was slowly cooled to room temperature and washed with EtOAc. The aqueous phase was cooled in an ice bath and 50% NaOH solution was carefully poured onto the solution. As the pH approached neutrality, the solution became opaque. Base was added until pH~9, and the aqueous layer was extracted with EtOAc. The organic layer was washed consecutively with $H_2O$ and brine, and dried over sodium sulfate. Filtration and evaporation of the solvent yielded the crude imine product as an amber syrup. The reaction product was eluted with chloroform through a 1-inch pad of Al (reactivity III) to remove polar contaminants. The eluate was concentrated to a dark amber syrup, which was redissolved in EtOAc and a saturated solution of oxalic acid/EtOAc was added dropwise to the mixture. After trituration of the product in the acid solution, the oxalate salt precipitated from the solution and the solids collected by vacuum filtration. The pale yellow powder was recrystallized from isopropanol/MeOH as an off-white powder (2.8 g, 34%—over two steps).

NMR free base $^1H$ ($CDCl_3$): 1.86 (m, 2H, H-9a, 9b), 2.43 (t, $J_{8,9}$=8, 2H, H-8a, 8b), 3.68 (s, 2H, H-6a, 6b), 3.83 (m, 2H, H-10a, 10b), 7.26 (dd, $J_{3,4;\ 4,5}$=4, 1H, H-4), 7.59 (d, $J_{3,4}$=4, 1H, H-3), 8.49 (t, 2H, H-1, 5). free base $^{13}C$ ($CDCl_3$): 22.50 (C-6), 36.70 (C-9), 37.54 (C-8), 60.92 (C-10), 123.41 (C-4), 132.45 (C-2), 136.48 (C-3), 148.03 (C-5), 150.11 (C-1), 175.54 (C-7). (M+H)+ 161.11, m.p. oxalate 123° C.

3-(pyrrolidin-2-ylmethyl)pyridine (norhomonicotine) (5) To the oxalate salt of 4 (1.5 g, 6.0 mmol) dissolved in MeOH/AcOH (4:1) and stirring at −15° C. (ice/brine) was added excess NaBH$_4$ over a period of 30 minutes. The reaction continued to stir and was allowed to warm to ambient temperature overnight. To the reaction was added HCl until pH~2. The reaction mixture was washed with Et$_2$O, and the aqueous phase separated and basified with NaOH until pH~13. The aqueous phase was extracted with CHCl$_3$ and the organic layer separated and dried over sodium sulfate. After filtration, the solvent was evaporated and the residue taken up in EtOAc. To the product solution was added dropwise a solution of HBr in EtOH. The solution was concentrated by rotary evaporation (2×), which resulted in a powdery residue. The HBr salt of 3 was recrystallized from EtOH as an off-white powder (1.3 g, 91%).

NMR HBr $^1$H (MeOH): 1.86 (m, 1H, H-9a), 2.07 (m, 1H, H-9b), 2.17 (m, 1H, H-8a), 2.26 (m, 1H, H-8b), 3.28-3.57 (m, 4H, H-6a, 6b, 10a, 10b), 4.04 (m, 1H, H-7), 8.13 (dd, J$_{3,4}$=8, J$_{4,5}$=5.7, 1H, H-4), 8.71 (d, J$_{3,4}$=8, 1H, H-3), 8.85 (d, J$_{4,5}$=5.7, 1H, H-5), 9.04 (s, 1H, H-1). free base $^{13}$C (CDCl$_3$) 25.19 (C-9), 31.59 (C-8), 39.60 (C-6), 46.49 (C-10), 60.54 (C-7), 123.77 (C-4), 135.65 (C-2), 136.89 (C-3), 148.06 (C-5), 150.65 (C-1). Anal. Calc'd (2 HBr) C$_{10}$H$_{16}$N$_2$Br$_2$: C, 37.1; H, 5.0; N, 8.6. Found: C, 37.16; H, 4.82; N, 8.50, (M+H)+ 163.1240, m.p. HBr 195.4° C.

3-((1-(2-hydroxyethyl)pyrrolidin-2-yl)methyl)pyridine (8): To a solution of 3 (the free base, prepared above) (320 mg, 0.00198 M) in THF was added 0.33 mL (1.1 eq) of 2-benzyloxy acetaldehyde and the reaction mixture was allowed to stir at room temperature for approximately 30 min. in order to allow imine formation. To this mixture was added 0.63 grams (1.5 eq) of sodium triacetoxyborohydride and the reaction mixture was allowed to continue at room temperature and monitored by TLC for completion. After stirring overnight the reaction was judged complete, water was added and reaction was made acidic by addition of dilute sulfuric acid (10%) and concentrated to remove the THF. The residue was diluted with 50 mL of water and extracted with ethyl acetate to remove any un-reacted aldehyde. The aqueous layer was made strongly basic by the addition of 60% sodium hydroxide solution (10 mL) and extracted with ethyl acetate (2×). The ethyl acetate layers were combined and washed with brine, dried over anhydrous sodium sulfate, filtered and concentrated to give the crude protected 4, which was used without further purification. Crude protected 4 was dissolved in ethanol and subjected to catalytic hydrogenation over 5% Pd/C and 55 psi hydrogen pressure using a Parr shaker hydrogenation apparatus. After reaction completion, it was diluted with chloroform, filtered though Celite to remove the catalysis and concentrated to give 8. Other compounds may be synthesized by analogy following the general chemistry pathways as described above with reference to the specific chemistry described in the above examples.

Synthesis of Pyridylpiperidine Analogs (FIG. 3, Scheme 3)

N-(2-Hydroxyethyl)-N'-(3-pyridylmethyl)-piperazine HCl. A solution of N-2hydroxyethylpiperazine (3 g, 0.023 M) and 3-Pyridinecarboxaldehyde (3 g 0.028 M J.2 eq.) in 200 mL of THF (dried over 4 molecular sieves) was cooled with stirring in an Ice/Salt bath to −10. To the cooled solution was added sodium triacetoxyborohydride (3 g, 1.5 eq.) and the solution was allowed to stir and warm to room temperature over night. That this time the reaction was judged nearly complete by Thin Layer Chromatography. An additional 400 mg of sodium triacetoxyborohydride was added and stirring continued for 2 h. The reaction was quenched by the addition of 50 ml of 1% aqueous sulfuric acid. The reaction was concentrated to remove the THF, diluted with water and extracted with ethyl acetate. The aqueous layer was made strongly basic (pH=10) with 60% sodium hydroxide solution and extracted three times (200 ml) with ethyl acetate. The ethyl acetate layers were combined, washed with brine, dried over anhydrous sodium sulfate, filtered and concentrated under reduced pressure to give the crude product as an oil. The oil was dissolved in absolute ethanol and concentrated hydrochloric acid was added until the pH was approximately 4. The ethanol was removed under reduced pressure, which caused the HCl salt to crystallize. The solid was recrystallized from hot isopropanol to give 5 g (66%) as the tri-HCl salt. Mp 238-239 C. Anal. Calcd for C$_{12}$H$_{19}$N$_3$O 3HCl: C, 43.57; H, 6.65; N, 12.71. Found: C, 43.40; H, 6.63; N, 12.62. $^1$H NMR: (DMSO-d$_6$) (400 MHz) 8: 3.31-3.84 (complex multiplet, 12H), 4.67 (s, 2H), 8.12 (m, 1H), 8.86 (d, J=7.84 Hz 1H), 9.00 (d, J=5.44 Hz, 1H), 9.12 (s, H).

N-(2-Hydroxyethyl)-N'-(2-pyridylmethyl)-piperazine HCl. A solution of N-2 hydroxyethylpiperazine (3 g, 0.023 M) and 2-Pyridinecarboxaldehyde (3 g 0.028 M J.2 eq.) in 250 mL of THF (dried over 4A molecular sieves) was cooled with stirring in an Ice/Salt bath to −10'. To the cooled solution was added sodium triacetoxyborohydride (3 g, 1.5 eq.) and the solution was allowed to stir and warm to room temperature over night. That this time the reaction was judged nearly complete by Thin Layer Chromatography. An additional 400 mg of sodium triacetoxyborohydride was added and stirring continued for 2 h. The reaction was quenched by the addition of 50 ml of 1% aqueous sulfuric acid. The reaction was concentrated to remove the THF, diluted with water and extracted with ethyl acetate. The aqueous layer was made strongly basic (pH 10) with 60% sodium hydroxide solution and extracted three times (200 ml) with ethyl acetate. The ethyl acetate layers were combined, washed with brine, dried over anhydrous sodium sulfate, filtered and concentrated under reduced pressure to give the crude product as an oil. The oil was dissolved in absolute ethanol and concentrated hydrochloric acid was added until the pH was approximately 4. The ethanol was removed under reduced pressure, which caused the HCl salt to crystallize. The solid was recrystallized from hot isopropanol to give 4.5 g (60%) as the tri-HCl salt. Mp 210-211 C. Anal. Calcd for C$_{12}$H$_{19}$N$_3$O 3HCl H$_2$O: C, 41.31; H, 6.88; N, 12.05. Found: C, 41.58; H, 6.78; N, 12.12. $^1$HNMR: (DMSO-d$_6$) (400 MHz) 8: 3.28-3.80 (complex multiplet, 12H), 4.63 (s, 2H), 7.79 (m, 1H), 8.0 (d,J=7.79 Hz 1H), 8.31 (t,J=7.72 Hz, 1H), 8.83 (d,J=5.13 Hz, 1H).

N-(methyl)-N'-(3-pyridylmethyl)-piperazine HCl. A solution of N-methylpiperazine (1 g, 0.01 M) and 3-Pyridinecarboxaldehyde (1.3 g, 0.012 M, 1.2 eq.) in THF (dried over 4A molecular sieves) was cooled with stirring in an Ice/Salt bath to −10° C. To the cooled solution was added sodium triacetoxyborohydride (1.4 g, 1.5 eq.) and the solution was allowed to stir and warm to room temperature overnight. That this time the reaction was judged complete by Thin Layer Chromatography. The reaction was quenched by the addition of 50 ml of 1% aqueous sulfuric acid. The reaction was concentrated to remove the THF, diluted with water and extracted with ethyl acetate. The aqueous layer was made strongly basic (pH=10) with 60% sodium hydroxide solution and extracted three times (100 ml) with ethyl acetate. The ethyl acetate layers were combined, washed with brine, dried over anhydrous sodium sulfate, filtered and concentrated under reduced pressure to give the crude product as an oil. The oil was dissolved in absolute ethanol and concentrated hydrochloric acid was added until the pH was approximately 4. The ethanol was removed under reduced pressure, which caused the HCl salt to crystallize. The solid was recrystallized from hot ethanol to give 900 mg (30%) as the tri-HCl salt. Mp 242-243 C. Anal. Calcd for $C_{11}H_{17}N_3O$ 3HCl 1.5$H_2O$: C, 40.31; H, 7.02; N, 12.82. Found: C, 40.36; H, 7.01; N, 12.82. $^1$H NMR: (DMSO-$d_6$) (400 MHz) 8: 2.85 (s, 3H) 3.60 (broad multiplet, 8H), 4.61 (s, 2H), 8.0 (m, 1H), 8.81 (d, J=7.76 Hz 1H), 8.98 (d, J=5.43 Hz, 1H), 9.18 (s, 1H).

Synthesis of Scheme 4 Compounds 2-(N-methyl, N-methylphenylamino)ethan-1-ol (oxalate salt) (25)

One equivalent each of N-methylethanolamine (4.28 mL) and benzaldehyde (21, 5.42 mL) were added to a 250 mL round-bottom flask containing 25 mL of 1,2-dichloroethane (DCE). The reactants were stirred at room temperature for 1 hour and then 1.5 equivalents (16.94 g) of NaBH(OAc)$_3$ were added. Stirring was continued until TLC showed the absence of all starting materials, about 12 hours. The reaction was quenched by adding aqueous bicarbonate and stirred for 15 minutes. The solvent was removed under reduced pressure and 10% $H_2SO_4$ was added to the remaining oil. This was extracted with ethyl acetate and the organic layer was discarded. The pH of the water layer was changed to a slightly basic pH with $K_2CO_3$ and extracted again with ethyl acetate. The organic layer was dried over sodium sulfate and concentrated to a small volume. The resulting free base was converted to an oxalate salt (25) and recrystallized from isopropanol, 6.162 g, 45.29%.

m.p. 109-110° C. Anal. Calcd. for $C_{12}H_{17}O_5N$: C, 56.46; H, 6.71; N, 5.49. Found: C, 56.32; H, 6.66; N, 5.56. $^1$H NMR: δ 7.61 (m, 2H), 7.52 (m, 3H), 4.95 (bs, 1H), 4.34 (s, 2H), 3.83 (t, J=5.36 Hz, 2H), 3.21 (t, J=5.37 Hz, 2H), 2.75 (s, 3H). $^{13}$C NMR: δ 165.14, 131.35, 129.53, 129.09, 59.43, 56.75, 55.94, 40.07.

2-(N-methyl, N-methyl-4'-fluorophenylamino)ethan-1-ol (oxalate salt) (26)

A mixture of N-methylethanolamine (1.07 mL) and 22 (1.43 mL) were stirred together in DCE for 1 hour, then 4.23 g of NaBH(OAc)$_3$ was added and stirring continued for 12 hours. Workup proceeded as described above. Yield: 2.48 g of 26 as the oxalate salt, 68.1%.

m.p. 140-143° C. Anal. Calcd. for $C_{12}H_{16}O_5NF$: C, 52.74; H, 5.90; N, 5.13. Found: C, 52.78; H, 5.92; N, 5.19. $^1$H NMR: δ 7.58 (m, 2H), 7.28 (m, 2H), 4.91 (bs, 1H), 4.24 (s, 2H), 3.73 (t, J=5.36 Hz, 2H), 3.02 (t, J=5.37 Hz, 2H), 2.65 (s, 3H). $^{13}$C NMR: δ 165.07, 162.84 ($J_{C-F}$=245.97 Hz), 133.71, 133.63, 127.83, 116.05, 115.84, 58.54, 56.72, 55.99, 40.41.

2-(N-methyl, N-methyl-3'-fluorophenylamino)ethan-1-ol (HBr salt) (27)

A mixture of N-methylethanolamine (2.14 mL) and 23 (2.82 mL) were stirred together in DCE for 1 hour, then 8.46 g of NaBH(OAc)$_3$ was added and stirring was continued for 12 hours. Workup proceeded as described for compound 27. Yield: 5.695 g of 4.12 as the HBr salt, 89.3%.

m.p. 116-119° C. Anal. Calcd. for $C_{10}H_{15}ONFBr$: C, 45.45; H, 5.68; N, 5.30. Found: C, 45.40; H, 5.70; N, 5.29. $^1$H NMR: δ 7.51 (m, 4H), 5.45 (bs, 1H), 4.48 (s, 2H), 3.89 (t, J=5.26 Hz, 2H), 3.24 (t, J=5.24 Hz, 2H), 2.88 (s, 3H). $^{13}$C NMR: δ 162.29 ($J_{C-F}$=244.24 Hz), 136.17, 131.27 ($J_{C-F}$=8.44 Hz), 127.86, 118.37 ($J_{C-F}$=22.21 Hz), 116.86 ($J_{C-F}$=20.82 Hz), 58.44, 56.62, 55.37, 40.12.

2-(N-methyl, N-methyl-3-pyridoamino)ethan-1-ol (oxalate salt) (28)

A mixture of N-methylethanolamine (1.07 mL) and 24 (1.26 mL) were stirred together in DCE for 1 hour, then 4.23 g of NaBH(OAc)$_3$ was added and stirring was continued for 12 hours. Workup proceeded as previously described, except that the pH flip was unnecessary. Yield: 0.399 g of 28 as an oxalate salt, 11.71%.

m.p. 119-124° C. Anal. Calcd. for $C_{13}H_{18}O_9N_2$: C, 45.11; H, 5.29; N, 8.10. Found: C, 44.93; H, 5.27; N, 8.01. $^1$H NMR: δ 8.83 (m, 2H), 8.14 (d, J=7.79 Hz, 1H), 7.66 (m, 1H), 5.41 (bs, 1H), 4.54 (s, 2H), 3.91 (t, J=5.05 Hz, 2H), 3.28 (t, J=5.04 Hz, 2H), 2.89 (s, 3H). $^{13}$C NMR: δ 162.82, 152.26, 150.78, 139.51, 126.49, 124.17, 56.67, 56.59, 55.49, 39.81.

2-(N-methyl, N-methylphenylamino)ethyl acetate (oxalate salt) (29)

One equivalent of 25 (1.0 g), 3 equivalents of sodium acetate (0.96 g) and 20 mL of dichloroethylene were added to a 250 mL round-bottom flask along with 25 mL of DCE. The reaction was stirred for 30 minutes at room temperature, at which time 1.5 equivalents (0.6 mL) of acetic anhydride were added. The mixture was stirred at room temperature until TLC indicated completion of reaction (about 12 hours). The reaction was quenched with ice, then extracted with ethyl acetate. The organic layer was washed twice with both aqueous bicarbonate and distilled water, then dried over sodium sulfate and concentrated. The resulting free base was converted into an oxalate salt and recrystallized from isopropanol, to give 0.84 g, (71.9%) of 29.

m.p. 109-113° C. Anal. Calcd. for $C_{14}H_{19}O_6N$: C, 56.56; H, 6.44; N 4.71. Found: C, 56.57; H, 6.42; N, 4.79. $^1$H NMR: δ 7.54 (m, 5H), 5.00 (bs, 1H), 4.39 (t, J=5.35 Hz, 2H), 4.20 (s, 2H), 3.21 (t, J=5.34 Hz, 2H), 2.65 (s, 3H), 2.13 (s, 3H). $^{13}$C NMR: δ 168.95, 162.77, 131.50, 129.24, 127.49, 58.30, 58.01, 52.25, 38.43, 19.44.

2-(N-methyl, N-methyl-4'-fluorophenylamino)ethyl acetate (oxalate salt) (30)

Above procedure was followed with 1.0 g of 26, 0.9 g of NaOAc, and 0.5 mL acetic anhydride. 1.03 g of 30 was isolated as an oxalate salt, 88.93%.

m.p. 135-138° C. Anal. Calcd. for $C_{14}H_{18}O_6NF$: C, 53.33; H, 5.75; N, 4.44. Found: C, 53.30; H, 5.72; N, 4.52. $^1$H NMR: δ 7.51 (m, 2H), 7.25 (m, 2H), 5.49 (bs, 1H), 4.27 (t, J=5.34 Hz, 2H), 4.06 (s, 2H), 3.07 (t, J=5.32 Hz, 2H), 2.52 (s, 3H), 2.03 (s, 3H). $^{13}$C NMR: δ 170.51, 164.10, 162.52 ($J_{C-F}$=245.01 Hz), 132.93, 132.85, 126.52, 115.88, 115.67, 59.71, 59.05, 53.84, 40.44, 21.01.

2-(N-methyl, N-methyl-3'-fluorophenylamino)ethyl acetate (maleate salt) (31)

The procedure described in 27 was repeated with 2.58 g of 4.12, 2.21 g of NaOAc, and 1.27 mL of acetic anhydride. 1.652 g of 31 was isolated as a maleate salt, 69.0%.

m.p. 114-116° C. Anal. Calcd. for $C_{16}H_{20}O_6NF$: C, 56.30; H, 5.91; N, 4.10. Found: C, 56.13; H, 5.82; N, 4.18. $^1$H NMR: δ 7.25 (m, 1H), 7.08 (m, 2H), 6.93 (m, 1H), 4.18 (t, J=5.81 Hz, 2H), 3.54 (s, 2H), 2.64 (t, J=5.81 Hz, 2H), 2.28 (s, 3H), 2.05 (3, 3H). $^{31}$C NMR: δ 171.38, 163.31 ($J_{C-F}$=245.24 Hz), 141.82, 130.02 ($J_{C-F}$=8.17 Hz), 124.73 ($J_{C-F}$=1.98 Hz), 115.96 ($J_{C-F}$=21.33 Hz), 114.33 ($J_{C-F}$=21.17 Hz), 62.37, 62.13, 55.59, 42.84, 21.29.

Biological Data

General Methods

Cell Culture: PC12 cells were maintained in 150-cm$^2$ tissue-culture flasks in Dulbecco's Modified Eagles medium containing 7% horse serum, 7% fetal calf serum, 1% non-essential amino-acids and 1% streptomycin (DMEM). The cells were incubated at 37 C in a 5% CO$_2$-enriched, humidified atmosphere. To attain maximum differentiation, the cells were maintained in DMEM.NGF medium for 7 days, with the medium being changed every 2 or 3 days.

Assay for Cell viability. Cells were dissociated by trituration and plated at 1×10$^4$ cells per well on poly-L-lysine coated 96 well plates containing DMEM.NGF media. Next, the differentiated cells were incubated with the test drug at different concentrations for the specified period of time. Cell viability (cytotoxicity) was determined using the Cell Titer 96 non-radioactive cell proliferation/cytotoxicity assay kit (Promega), which is based on the cellular conversion of a 3-(4,5-dimethylthiazol-2-yl)-2,5-diphenyltetrazolium bromide (MTT) into a formazan product which can be detected spectrophotometrically. After deprivation of cells from NGF and serum, the medium was aspirated and 15 l of dye solution dissolved in DMEM was added. After an additional 4 hr incubation at 37 C, 100 l of solubilization/stop solution was added and the absorbance of solubilized MTT formazan products was measured at 570 nm.

Binding assay: PC-12 cells were plated at 100,000 cells per well on poly-L-lysine coated 24 well plates containing DMEM.NGF solution. To attain maximum differentiation, culture medium was replaced every 48-72 hours with fresh DMEM.NGF solution, and the cells were maintained for 7 days. Saturation binding studies were performed with [$^{125}$I]-bungarotoxin concentration ranging from 0.1 nM to 10 nM to obtain ligand Kd. Competition binding assays were performed with 10-15 concentrations of each analog. For the binding studies, the culture medium was removed and replaced with medium containing an analog, and 2 nM [$^{125}$I]-bungarotoxin. The non-specific binding was determined in the presence of 1 M unlabeled-bungarotoxin, which was added prior to the [$^{125}$I]-bungarotoxin. The cells were incubated for 2 hr at 37 C and rinsed four times with 2 ml aliquots of HEPES solution (137 mM NaCl, 5.4 mM Kcl, 0.8 mM MgSO$_4$, 0.9 mM NaPO$_4$, 0.4 mM K$_2$PO$_4$, 1.8 mM CaCl$_2$, 2 mg/ml BSA, and 10 mM HEPES, pH 7.4). After washing, cells were detached from the plate by addition of 1 ml of 1N NaOH. Bound radioactivity was quantified by gamma counting. Nonspecific binding, determined in the presence of excess unlabelled—bungarotoxin, was subtracted from total binding to yield specific binding. Results were normalized to total protein, which was assayed as follows: the cells were scraped in 2% SDS/0.1N NaOH solution and the BCA protein assay was conducted with BSA as a standard. $K_i$ values were calculated using the Cheng and Prusoff equation: $K_i$=IC50/(1+[L]/$K_d$) (where [L] is th concentration of radioligand. See Cheng and Prusoff, Biochem. Pharmacol. 23, 3099-3108, 1973.

Findings

Figure 5:
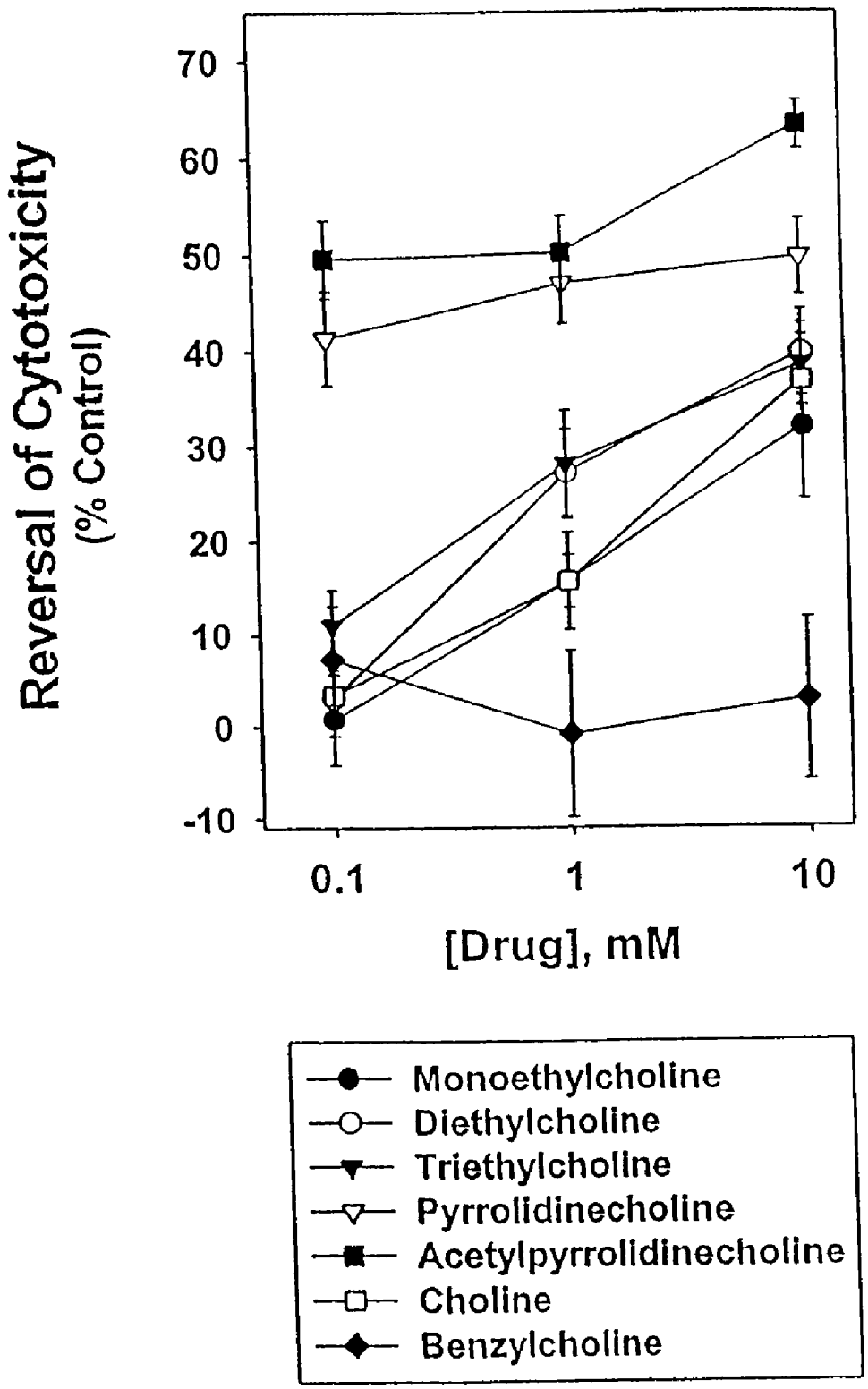
FIG. 5 shows the results of the MTT assay from the experimental section under control conditions, and in cultures in which a choline analog was introduced into the medium at the time of neurotrophic factor withdrawal. The data for choline and 6 other analogs are presented.

Differentiated PC-12 cells were deprived of neurotrophic factors for 24 hr to promote cytotoxicity. Cell viability was measured by the MTT assay under control conditions, and in cultures in which a choline analog was introduced into the medium at the time of neurotrophic factor withdrawal. The data for choline and 6 other analogs are presented in FIG. 5.

The analog benzylcholine did not affect cell viability. Choline and its mono-, di-, and tri-ethyl analogs produced a concentration dependent and intermediate level of neuroprotection improving cell viability by up to 40% of baseline. The analogs pyrrolidinecholine and acetylpyrrolidinecholine were most effective, improving cell viability by over 60% of baseline. In fact, these two analogs were more potent as well, since the effects produced by the lowest dose tested (0.1 mM) were not that much reduced from the effects attributed to the 10 mM concentration.

Figure 6:
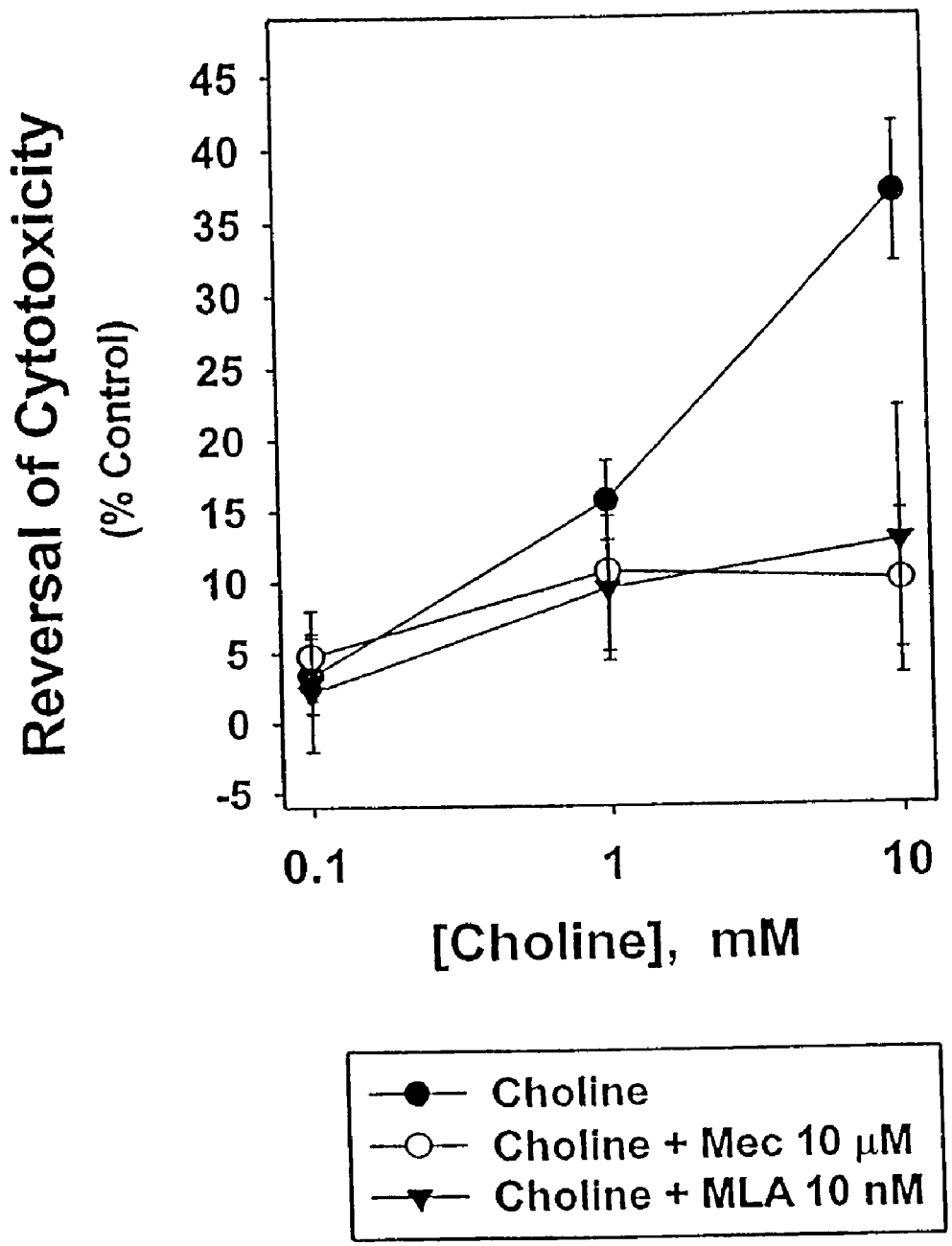
FIG. 6 shows the results of data from the MTT reduction assay from the experimental section. As indicated, co-administration of choline and the non-selective antagonist mecamylamine resulted in a significant (and almost complete) inhibition of choline's neuroprotective action. A similar finding was obtained for those experiments in which the antagonist, MLA, was used.

Since choline may serve as a natural ligand for the 7 subtype of the nicotinic acetyl choline receptor, and since stimulation of the 7 subtype by nicotine is known to produce a neuroprotective effect, we next sought to determine whether the neuroprotective effects produced by choline could be blocked by nicotinic receptor antagonists. The data are presented in FIG. 6. Co-administration of choline and the non-selective antagonist mecamylamine resulted in a significant (and almost complete) inhibition of choline's neuroprotective action. A similar finding was obtained for those experiments in which the 7 subtype preferring antagonist, MLA, was used.

Figure 7:
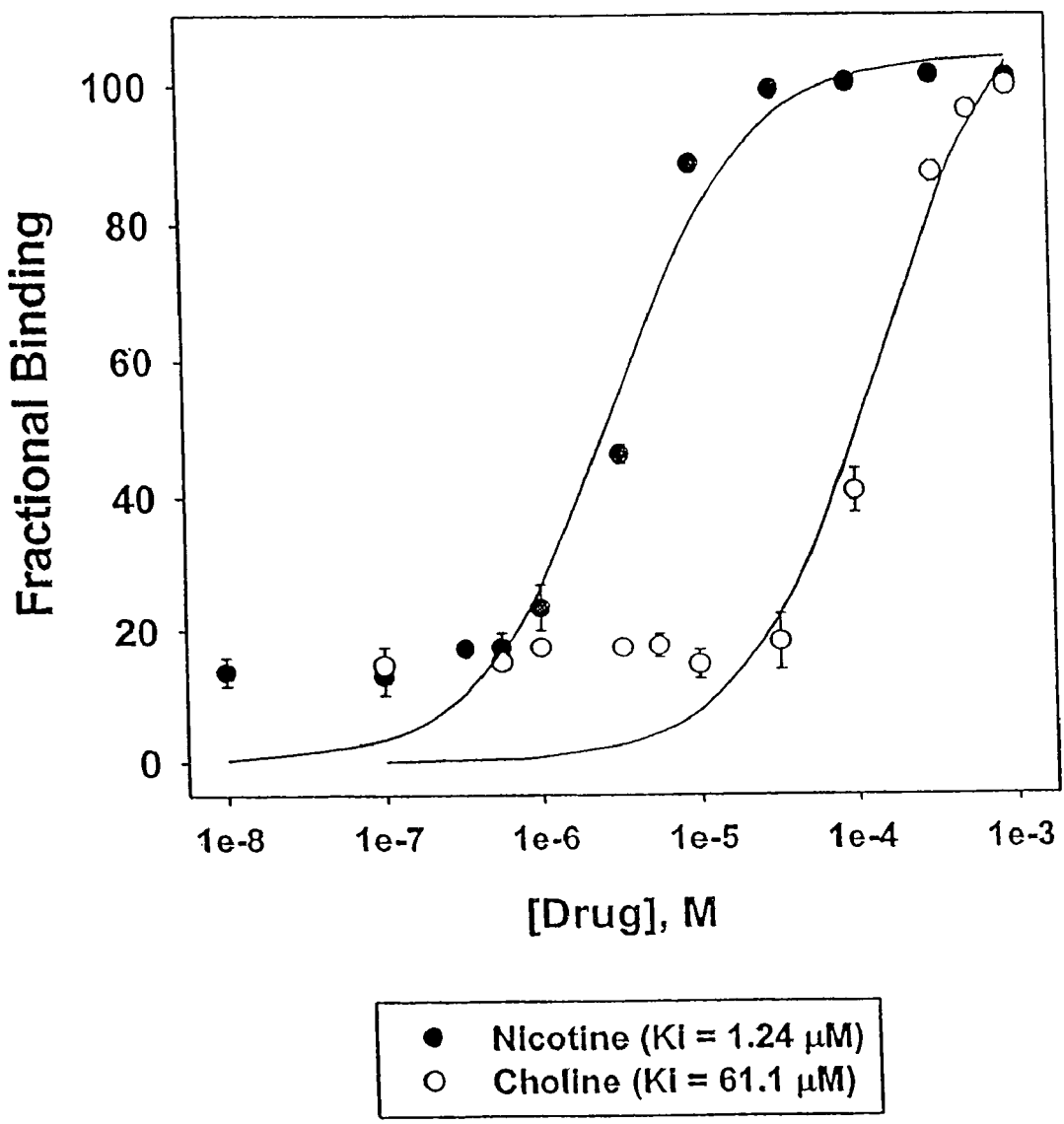
FIG. 7 shows an experiment which measured the ability of choline to displace the cell surface binding of [$^{125}$I]-bungarotoxin (a selective 7 nicotinic acetylcholine receptor antagonist) to differentiated PC-12 cells. These data are presented along with the displacement curve for nicotine as a comparison.

Since the neuroprotective action to choline appeared to be mediated through stimulation of cell surface 7 nicotinic actyl-choline receptors, we measured the ability of choline to displace the cell surface binding of [$^{125}$I]-bungarotoxin (a selective 7 nicotinic acetylcholine receptor antagonist) to differentiated PC-12 cells. These data are presented in FIG. 7 along with the displacement curve for nicotine as a comparison. Choline was only 50 fold less potent than nicotine in displacing [$^{125}$I]-bungarotoxin.

Figure 8:
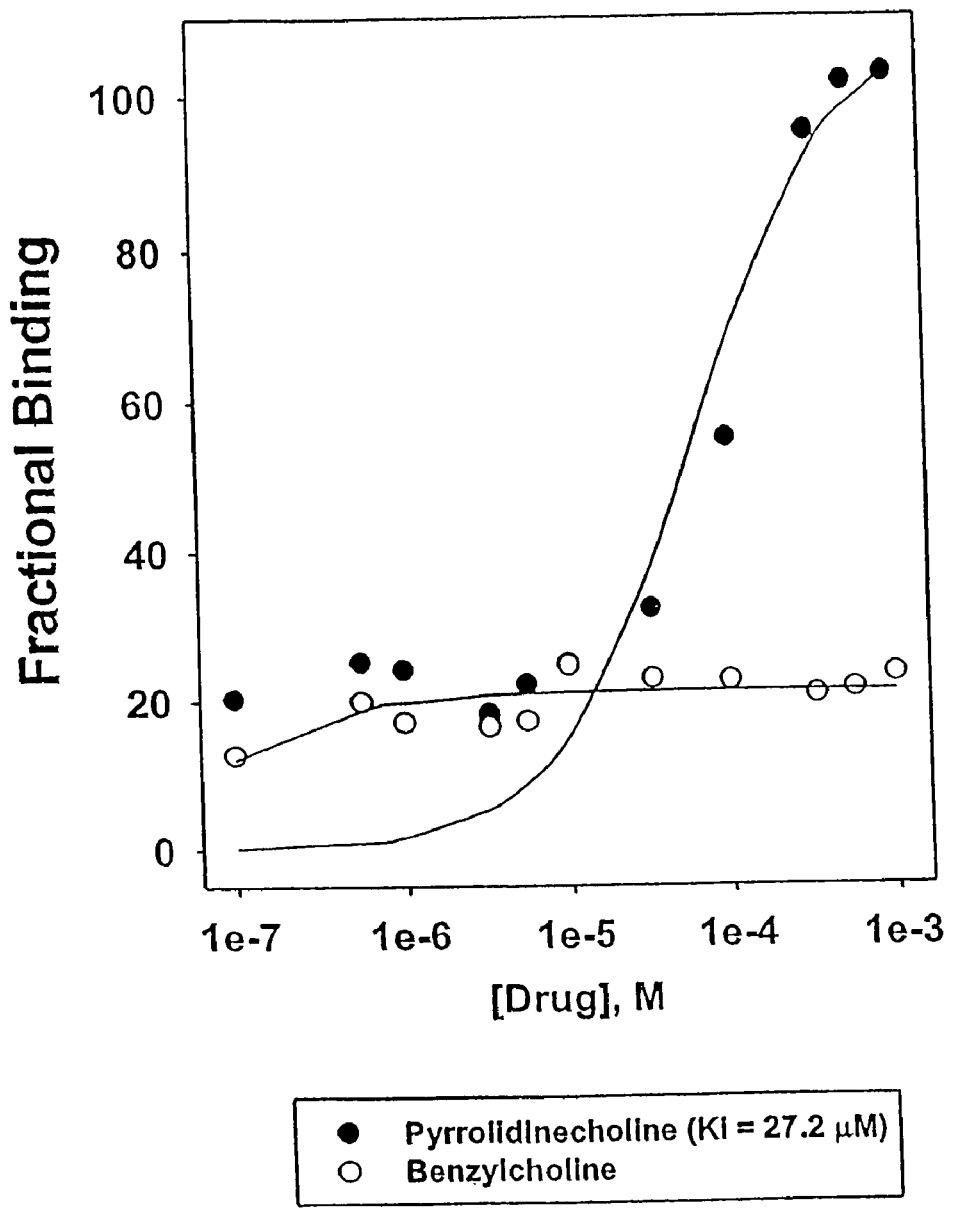
FIG. 8 shows an experiment which measured the ability of pyrrolidinecholine, an active choline analog, compared with benzylcholine, the inactive choline analog in the neuroprotection assay, for their ability to displace the cell surface binding of [$^{125}$I]-bungarotoxin to PC-12 cells.
Figure 9:
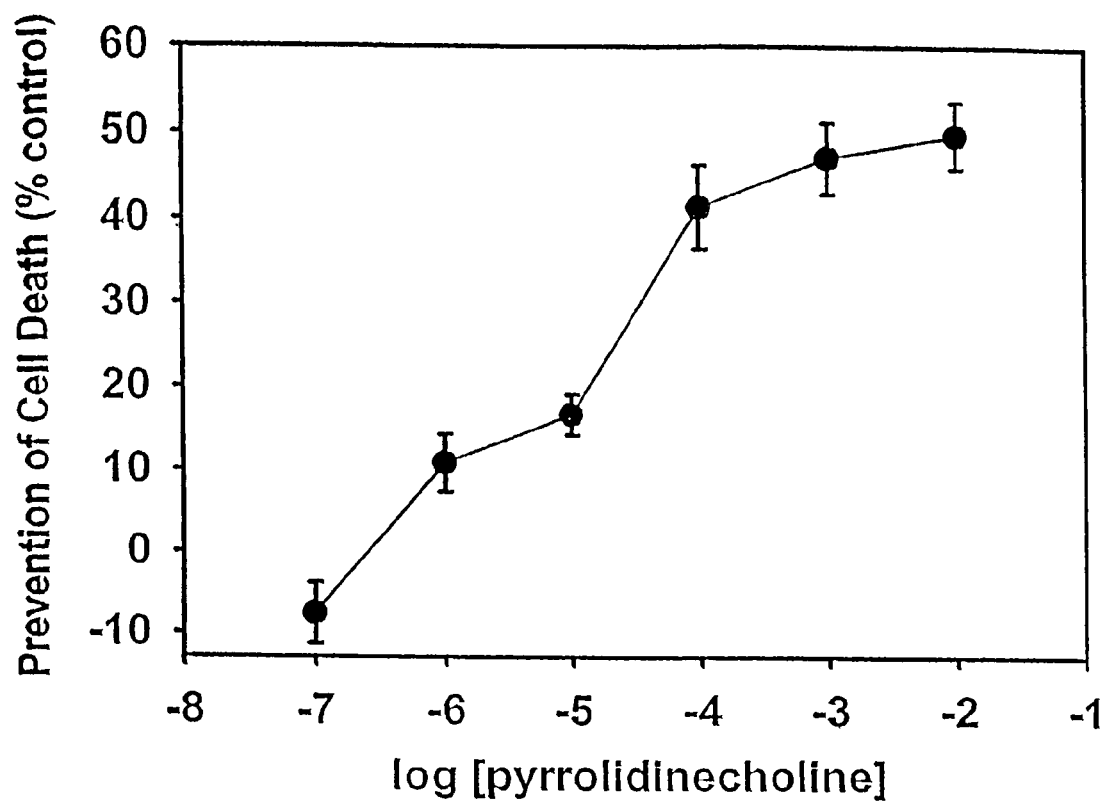
FIGS. 9 and 10, show that the neuroprotective action of pyrrolidinecholine (like choline) (FIG. 9) was blocked by pretreatment with either mecamylamine (10 M) or MLA (10 nM) (FIG. 10).
Figure 10:
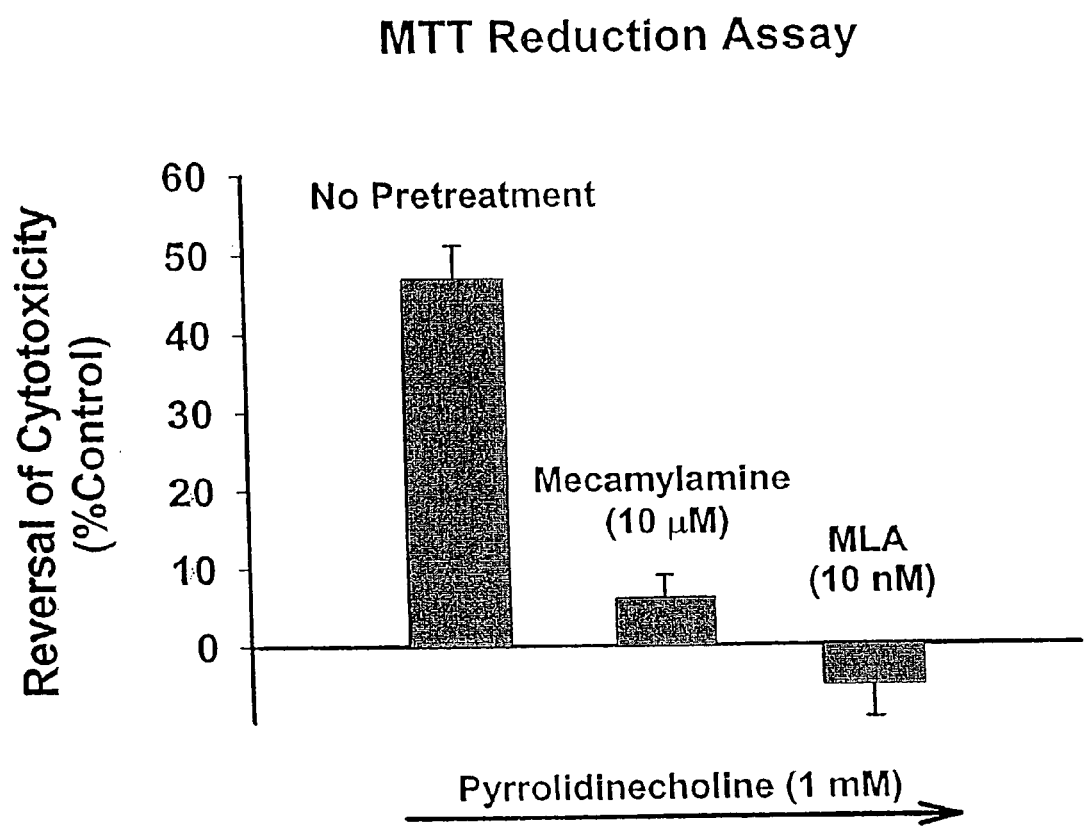

Next, pyrrolidinecholine, the most active choline analog, was compared with benzylcholine, the inactive choline analog in the neuroprotection assay, for their ability to displace the cell surface binding of [$^{125}$I]-bungarotoxin to PC-12 cells. As indicated in FIG. 8, the inactive analog (for neuroprotection), benzylcholine also failed to significantly interact with [$^{125}$I]-bungarotoxin binding sites. In contrast, pyrrolidinecholine fully displaced [$^{125}$I]-bungarotoxin binding, and it exhibited a slightly more potent affinity for the site than did choline which fits with pyrrolidinecholine's greater activity in the neuroprotrection assay. As indicated in FIGS. 9 and 10, the neuroprotective action of pyrrolidinecholine (like choline) (FIG. 9) was blocked by pretreatment with either mecamylamine (10 M) or MLA (10 nM) (FIG. 10).

Further Experiments

Cytoprotective Effect of Choline and Compounds According to the Present Invention Cytoprotective effect of nicotine in differentiated PC-12 cells. Differentiated PC-12 cells described above were exposed to the indicated concentrations of nicotine 24 hours (see FIG. 11) prior to growth factor withdrawal (removal of nerve growth factor and changing from serum-containing to serum-free medium. % Protection values were calculated as the ratio of ELISA-based absorbance values for [protected cells–deprived cells (no nicotine):control (non-deprived) cells–deprived cells]×100. Each point represents data obtained from two separate assays each performed with 5-8 replicates per point. Note the biphasic nature of the concentration-effect curve in FIG. 11.

Cytoprotective Effect of Choline Analogs in Differentiated PC-12 Cells.

Figure 11:
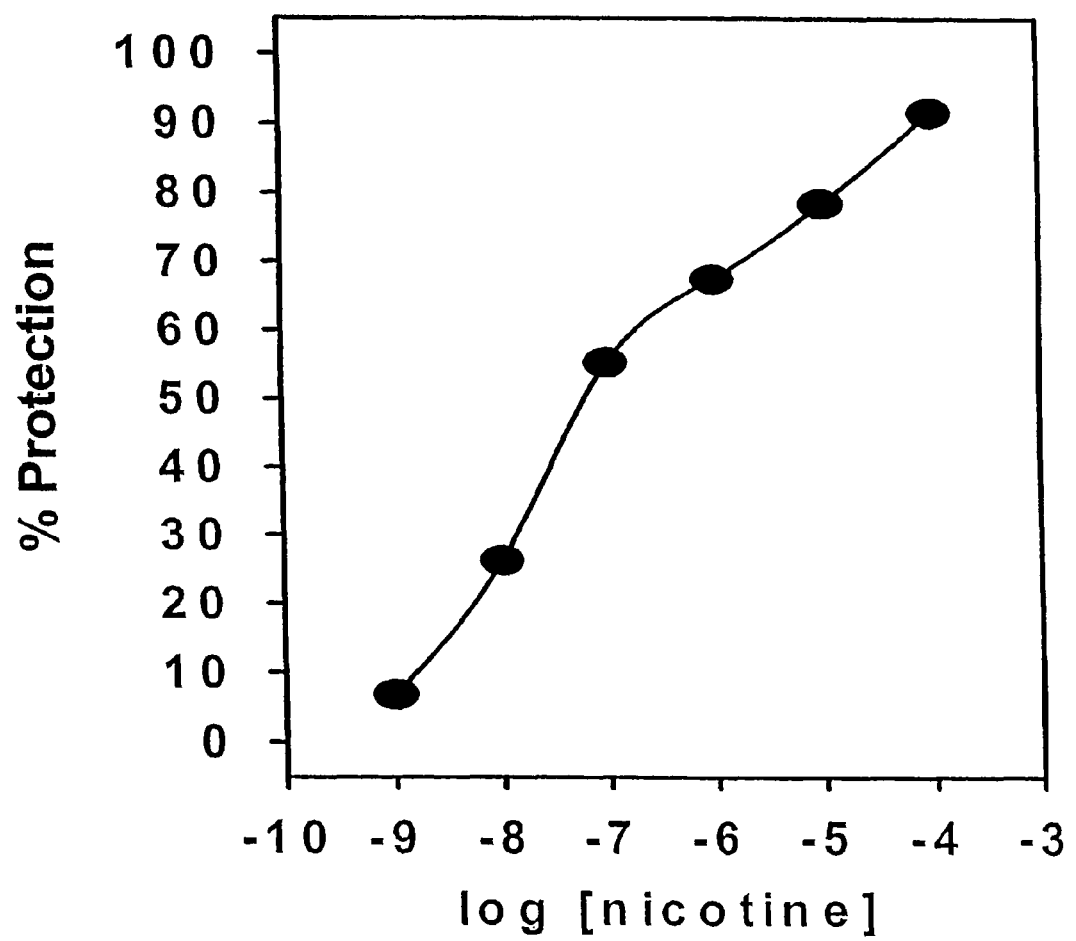
FIG. 11 shows the cytoprotective effect of nicotine in differentiated PC-12 cells. The % Protection values presented were calculated as the ratio of ELISA-based absorbance values for [protected cells–deprived cells (no nicotine):control (non-deprived) cells–deprived cells]×100.
Figure 12:
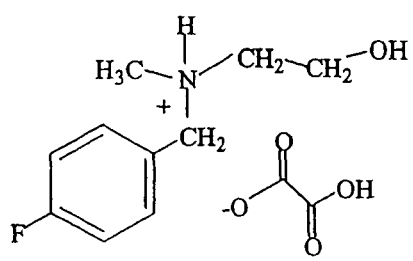
FIG. 12 shows a number of compounds according to the present invention as pharmaceutically acceptable salts.
Figure 12:
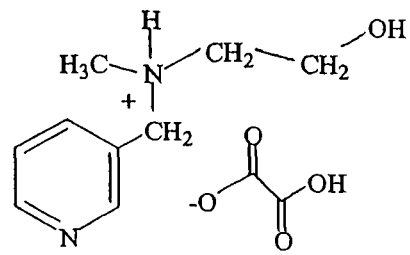
Figure 12:
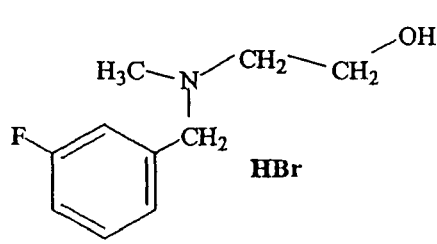
Figure 12:
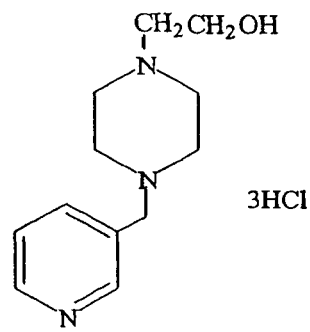
Figure 12:
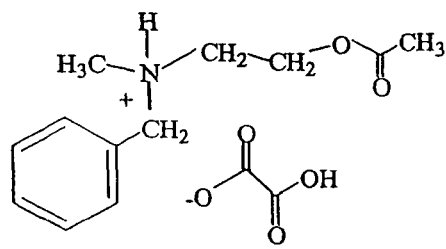
Figure 12:
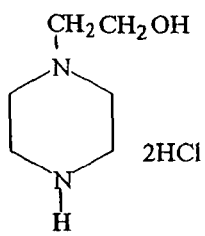
Figure 12:
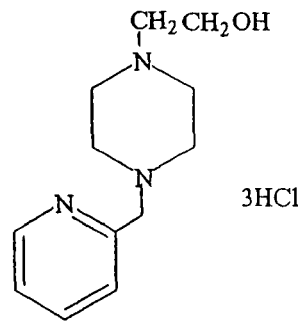
Figure 13A:
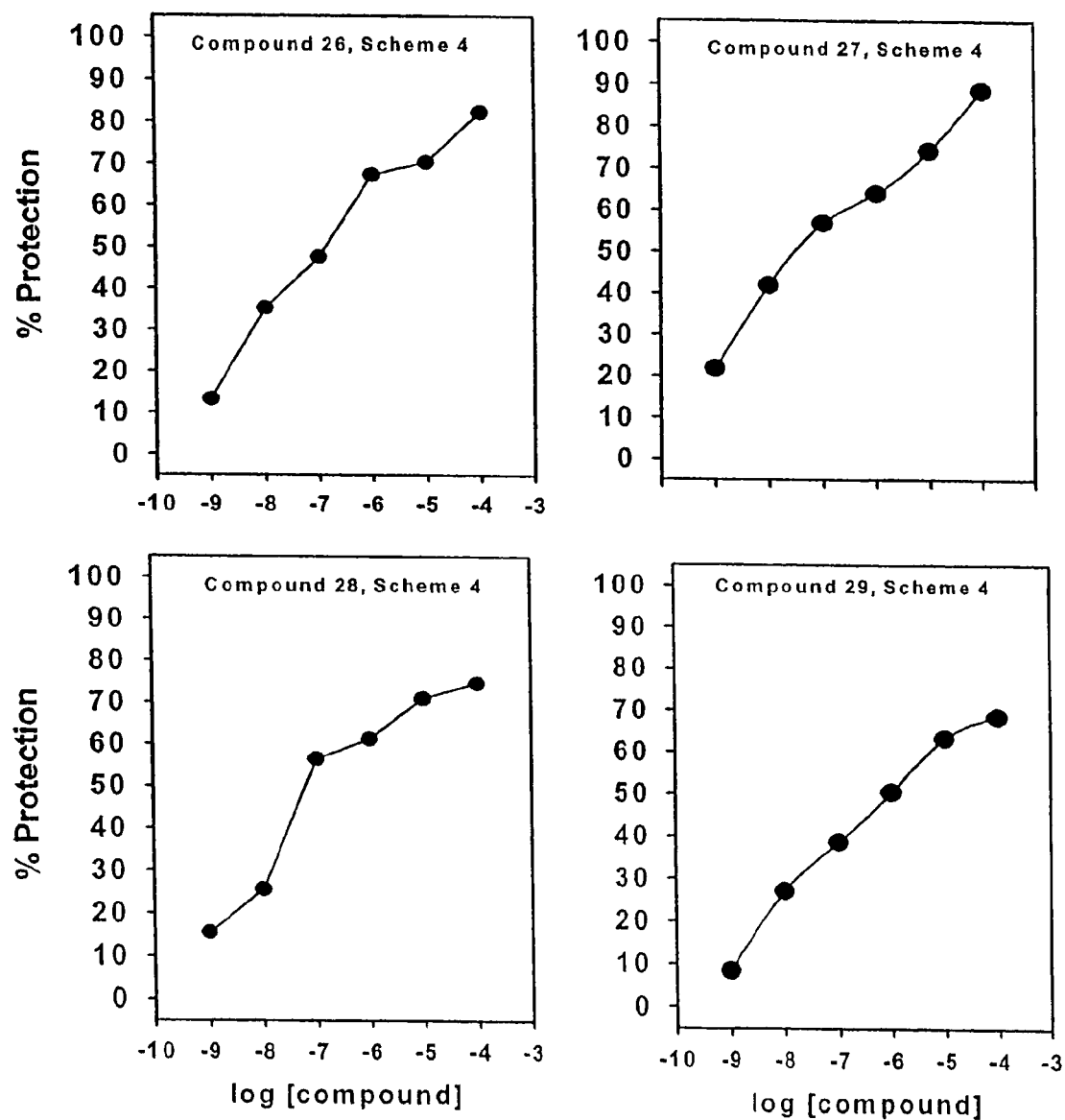
FIGS. 13A and B show the cytoprotective effect of nicotine analogs in differentiated PC-12 cells.
Figure 13B:
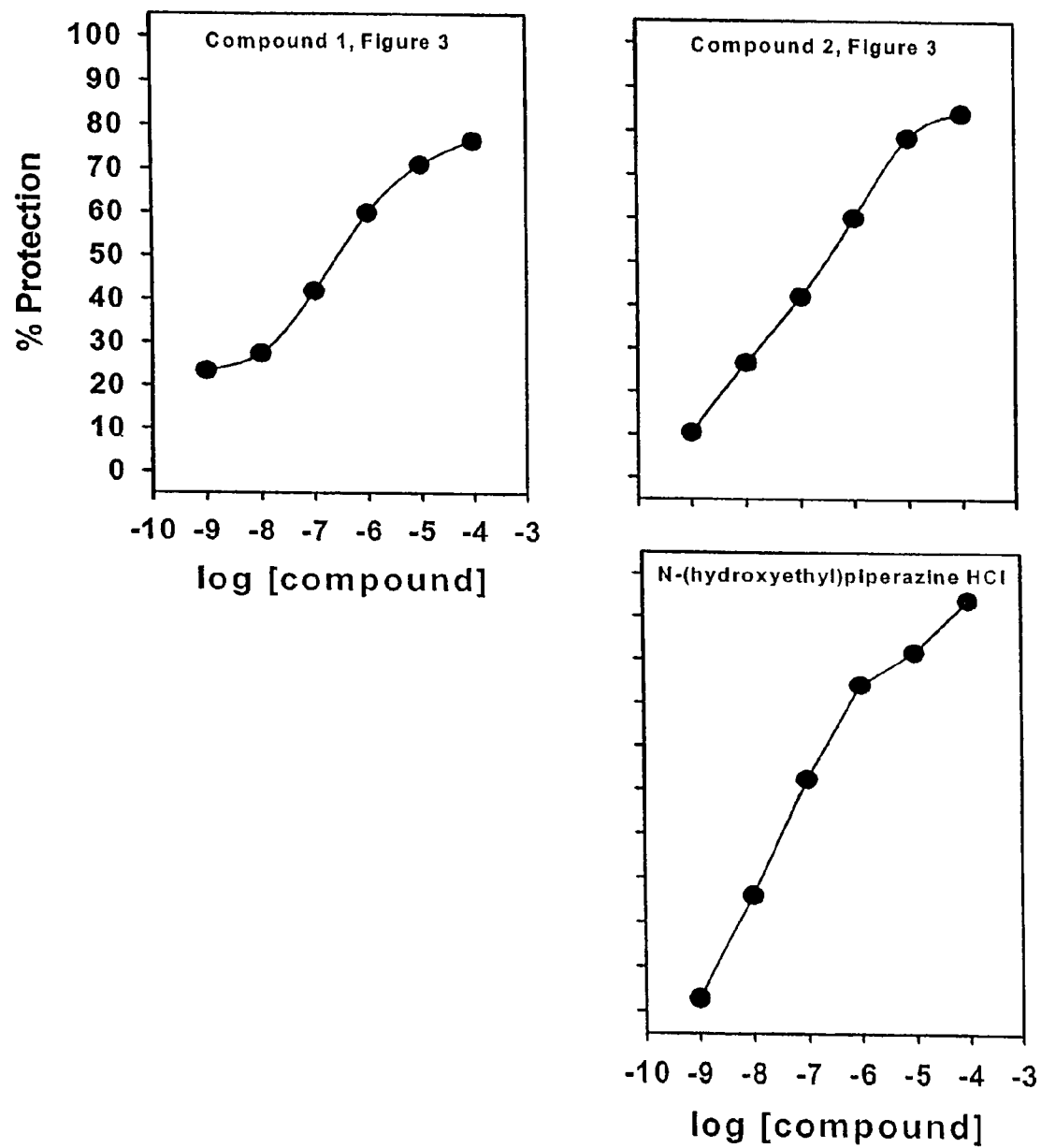

The above-described differentiated PC-12 cells were exposed to the indicated concentrations (see FIGS. 13A and B) of the FIG. 12 choline analogs 24 hours prior to growth factor withdrawal (removal of nerve growth factor, and changing from serum-containing to serum-free medium). % Protection values were calculated as the ratio of ELISA-based absorbance values for [protected cells−deprived cells (no analog):control (non-deprived) cells−deprived cells]×100. Each data point in FIG. 13 represents data obtained from two separate assays each performed with 5-8 replicates per point. Note that Compound 27, and Compound 2 provide results similar to nicotine (FIG. 11).

It is to be understood by those skilled in the art that the foregoing description and examples are illustrative of practicing the present invention, but are in no way limiting. Variations of the detail presented herein may be made without departing from the spirit and scope of the present invention as defined by the following claims.

The invention claimed is:

1. A compound according to the chemical structure:

[Structure II with $R^2$, $R^1$, $R^3$]

[Structure III with $R^2$, $R^1$]  or

[Structure IV with $R^2$, $R^1$]

wherein each $R^1$ is a

[pyridyl-Z- group]  or  [4-pyridyl-Z- group];

Z is —$(CH_2)_n$—  or  —CH=CH—$(CH_2)_n$—;

$R^2$ is H, a $C_1$ to $C_{12}$ straight, branch-chained or cyclic saturated or unsaturated hydrocarbon, a $(CH_2)_k OR^5$ group or a group $R^1$ as described above;

$R^3$ is a H, $C_1$ to $C_{12}$ alkyl group, a $C_2$ to $C_{12}$ alkenyl group or a $(CH_2)_k OR^5$ group;

$R^5$ is H, a $C_1$ to $C_{12}$ alkyl, a $C_2$ to $C_{12}$ alkenyl group or carboxylic acid, a $C_2$ to $C_{12}$ acyl or alkyl ester group or a $C_3$ to $C_{12}$ alkylene ester group;

n is 0 to 12; and k is 1 to 12;

or a pharmaceutically acceptable salt thereof.

2. The compound according to claim 1 wherein, n is 0 to 8 and or k is 1 to 8.

3. The compound according to claim 1 wherein $R^3$ is a $(CH_2)_k OR^5$ group.

4. The compound according to claim 1 wherein $R^5$ is H.

5. The compound according to claim 3 wherein $R^5$ is H and k is 1 to 8.

6. The compound according to claim 5 wherein k is 1 to 3.

7. The compound according to claim 5 wherein k is 2.

8. A pharmaceutical composition, comprising an effective amount of a compound according to the chemical structure:

[Structures with $R^2$, $R^1$, $R^3$] , , or wherein each $R^1$ is a

[pyridyl-Z- group]  or  [4-pyridyl-Z- group];

Z is —$(CH_2)_n$—  or  —CH=CH—$(CH_2)_n$—;

$R^2$ is H, a $C_1$ to $C_{12}$ straight, branch-chained or cyclic saturated or unsaturated hydrocarbon, a $(CH_2)_k OR^5$ group or a group $R^1$ as described above;

$R^3$ is a H, $C_1$ to $C_{12}$ alkyl group, a $C_2$ to $C_{12}$ alkenyl group or a $(CH_2)_k OR^5$ group;

$R^5$ is H, a $C_1$ to $C_{12}$ alkyl, a $C_2$ to $C_{12}$ alkenyl group or carboxylic acid, a $C_2$ to $C_{12}$ acyl or alkyl ester group or a $C_3$ to $C_{12}$ alkylene ester group;

n is 0 to 12; and k is 1 to 12;

or a pharmaceutically acceptable salt thereof, in combination with a pharmaceutically acceptable carrier, additive or excipient.

9. The composition according to claim 8 wherein n is 0 to 8 and or k is 1 to 8.

10. The composition according to claim 8 wherein $R^3$ is a $(CH_2)_k OR^5$ group.

11. The composition according to claim 8 wherein $R^5$ is H.

12. The composition, according to claim 10 wherein $R^5$ is H and k is 1 to 8.

13. The composition according to claim 12 wherein k is 1 to 3.

14. The composition according to claim 13 wherein k is 2.

15. A method of treating a patient having a neurodegenerative condition or other neurological condition selected from the group consisting of Parkinson's disease, Huntington's disease, amyotrophic lateral sclerosis, spinal muscular atrophy, Friedrich's ataxia, Pick's disease, Bassen-Kornzweig syndrome, Refsum's disease, retinal degeneration, Cruetzfelt-Jacob syndrome, dementia with Lewy bodies, and schizophrenia comprising administering to said patient an effective amount of a compound according to the chemical structure:

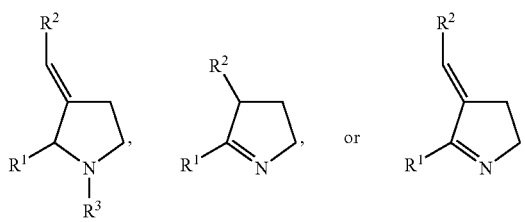

wherein each $R^1$ is a

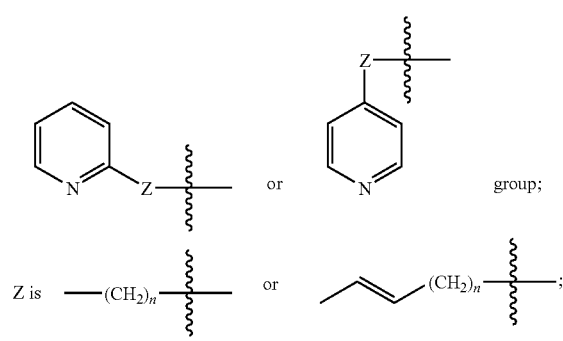

$R^2$ is H, a $C_1$ to $C_{12}$ straight, branch-chained or cyclic saturated or unsaturated hydrocarbon, a $(CH_2)_kOR^5$ group or a group $R^1$ as described above;

$R^3$ is a H, $C_1$ to $C_{12}$ alkyl group, a $C_2$ to $C_{12}$ alkenyl group or a $(CH_2)_kOR^5$ group;

$R^5$ is H, a $C_1$ to $C_{12}$ alkyl, a $C_2$ to $C_{12}$ alkenyl group or carboxylic acid, a $C_2$ to $C_{12}$ acyl or alkyl ester group or a $C_3$ to $C_{12}$ alkylene ester group;

n is 0 to 12; and k is 1 to 12;

or a pharmaceutically acceptable salt thereof, optionally in combination with a pharmaceutically acceptable carrier, additive or excipient.

16. The method according to claim 15 wherein n is 0 to 8 and or k is 1 to 8.

17. The method according to claim 15 wherein $R^3$ is a $(CH_2)_kOR^5$ group.

18. The method according to claim 15 wherein $R^5$ is H.

19. The method according to claim 17 wherein $R^5$ is H and k is 1 to 8.

20. The method according to claim 19 wherein k is 1 to 3.

21. The method according to claim 20 wherein k is 2.

22. A method of treating a patient having a neurodegenerative or neurological condition selected from the group consisting of Parkinson's disease, Huntington's disease, amyotrophic lateral sclerosis, spinal muscular atrophy, Friedrich's ataxia, Pick's disease, Bassen-Kornzweig syndrome, Refsum's disease, retinal degeneration, Cruetzfelt-Jacob syndrome, dementia with Lewy bodies, and schizophrenia comprising administering to said patient an effective amount of a compound according to the chemical structure:

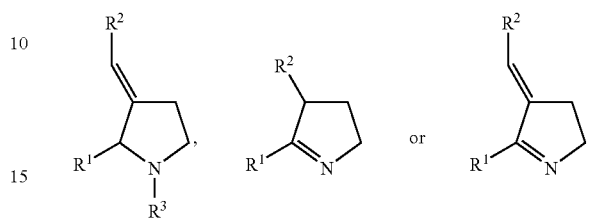

wherein each $R^1$ is a

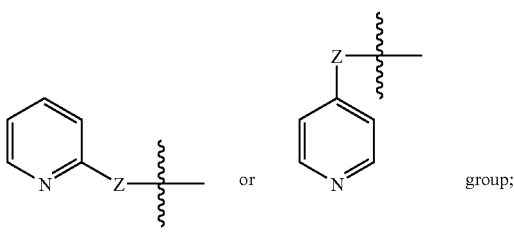

$R^2$ is H, a $C_1$ to $C_{12}$ straight, branch-chained or cyclic saturated or unsaturated hydrocarbon, a $(CH_2)_kOR^5$ group or a group $R^1$ as described above;

$R^3$ is a H, $C_1$ to $C_{12}$ alkyl group, a $C_2$ to $C_{12}$ alkenyl group or a $(CH_2)_kOR^5$ group;

$R^5$ is H, a $C_1$ to $C_{12}$ alkyl, a $C_2$ to $C_{12}$ alkenyl group or carboxylic acid, a $C_2$ to $C_{12}$ acyl or alkyl ester group or a $C_3$ to $C_{12}$ alkylene ester group;

n is 0 to 12; and k is 1 to 12;

or a pharmaceutically acceptable salt thereof, optionally in combination with a pharmaceutically acceptable carrier, additive or excipient.

23. The method according to claim 22 wherein it is 0 and k is 1-3.

24. The method according to claim 22 wherein $R^1$ is a group according to the chemical structure:

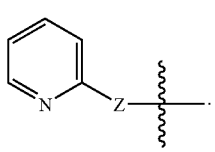

25. The method according to claim 22 wherein $R^1$ is a group according to the chemical structure:

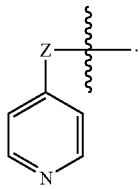

26. The method according to claim 22 wherein k is 1-2.

27. A method of treating a patient for a neurological or neurodegenerative condition selected from the group consisting of Parkinson's disease, Huntington's disease, amyotrophic lateral sclerosis, spinal muscular atrophy, Friedrich's ataxia, Pick's disease, Bassen-Kornzweig syndrome, Refsum's disease, retinal degeneration, Cruetzfelt-Jacob syndrome, dementia with Lewy bodies, and schizophrenia, comprising administering an effective amount of a compound according to the chemical structure:

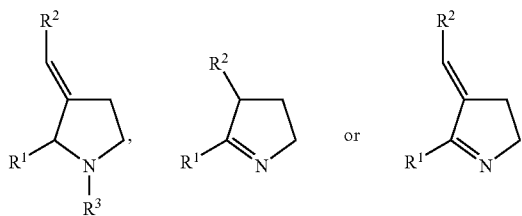

wherein each $R^1$ is a

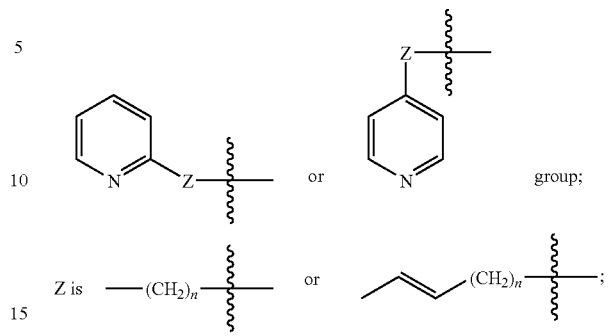 group;

$R^2$ is H, a $C_1$ to $C_{12}$ straight, branch-chained or cyclic saturated or unsaturated hydrocarbon, a $(CH_2)_kOR^5$ group or a group $R^1$ as described above;

$R^3$ is a H, $C_1$ to $C_{12}$ alkyl group, a $C_2$ to $C_{12}$ alkenyl group or a $(CH_2)_kOR^5$ group;

$R^5$ is H, a $C_1$ to $C_{12}$ alkyl, a $C_2$ to $C_{12}$ alkenyl group or carboxylic acid, a $C_2$ to $C_{12}$ acyl or alkyl ester group or a $C_3$ to $C_{12}$ alkylene ester group;

n is 0 to 12; and k 1 to 12;

or a pharmaceutically acceptable salt thereof, optionally in combination with a pharmaceutically acceptable carrier, additive or excipient.

* * * * *